(12) United States Patent
Colón et al.

(10) Patent No.: US 11,091,781 B2
(45) Date of Patent: Aug. 17, 2021

(54) CARBON FIXATION SYSTEMS AND METHODS

(71) Applicant: President and Fellows of Harvard College, Cambridge, MA (US)

(72) Inventors: Brendan Cruz Colón, Cambridge, MA (US); Chong Liu, Cambridge, MA (US); Marika Ziesack, Cambridge, MA (US); Pamela Ann Silver, Cambridge, MA (US); Daniel G. Nocera, Cambridge, MA (US)

( * ) Notice: Subject to any disclaimer, the term of this patent is extended or adjusted under 35 U.S.C. 154(b) by 0 days.

(21) Appl. No.: 16/793,577

(22) Filed: Feb. 18, 2020

(65) Prior Publication Data

US 2020/0255870 A1     Aug. 13, 2020

Related U.S. Application Data

(62) Division of application No. 15/758,843, filed as application No. PCT/US2016/051621 on Sep. 14, 2016, now Pat. No. 10,597,681.

(60) Provisional application No. 62/218,131, filed on Sep. 14, 2015.

(51) Int. Cl.
  *C12P 7/02*   (2006.01)
  *C25B 11/04*  (2021.01)
  *C25B 15/08*  (2006.01)
  *C25B 3/04*   (2006.01)
  *C25B 1/04*   (2021.01)
  *C25B 3/25*   (2021.01)

(52) U.S. Cl.
CPC ............ *C12P 7/02* (2013.01); *C25B 1/04* (2013.01); *C25B 3/25* (2021.01); *C25B 11/04* (2013.01); *C25B 15/08* (2013.01); *Y02E 60/36* (2013.01)

(58) Field of Classification Search
CPC ..... C12P 7/02; C25B 1/04; C25B 3/04; C25B 11/04; C25B 15/08; Y02E 60/36
See application file for complete search history.

(56) References Cited

U.S. PATENT DOCUMENTS

2012/0061237 A1*   3/2012   Brichese ............. C25B 11/0478
                                                            204/290.08

OTHER PUBLICATIONS

Torella et al. Efficient solar-to-fuels production from a hybrid microbial-water-splitting catalyst system. PNAS. Feb. 24, 2015. vol 112. No 8. pp. 2337-2342. (Year: 2015).*

* cited by examiner

*Primary Examiner* — Ciel P Contreras
(74) *Attorney, Agent, or Firm* — Wolf, Greenfield & Sacks, P.C.

(57) ABSTRACT

Systems and methods for fixing carbon using bacteria are described. In one embodiment, a system includes a reactor chamber with a solution contained therein. The solution may include hydrogen ($H_2$), carbon dioxide ($CO_2$), bioavailable nitrogen, and a chemolithoautotrophic bacteria. The system may also include a pair of electrodes that split water contained within the solution to form the hydrogen. Additionally, the system may be operated so that a concentration of the bioavailable nitrogen in the solution is below a threshold nitrogen concentration to cause the chemolithoautotrophic bacteria to produce a product.

36 Claims, 15 Drawing Sheets

Specification includes a Sequence Listing.

| Strain[a] | $E_{appl}$ (V) | Cathode\|Anode | V (mL)[b] | $C_{buffer}$ (mM)[c] | $\eta_{elec}$[d] | $\eta_{SCE}$[d] | Titer (mg/L) |
|---|---|---|---|---|---|---|---|
| H16 | 3.0 | NiMo\|CoP$_i$ | 100 | 36 | 5.0±0.6% | 0.9±0.1% | - |
| H16 | 2.7 | SS\|CoP$_i$ | 100 | 36 | 12±2% | 2.2±0.3% | - |
| H16 | 2.2 | NiMo\|CoP$_i$ | 100 | 36 | no growth | no growth | - |
| H16 | 2.2 | SS\|CoP$_i$ | 100 | 36 | no growth | no growth | - |
| H16 | 2.0 | NiMo\|CoP$_i$ | 100 | 36 | no growth | no growth | - |
| H16 | 2.0 | SS\|CoP$_i$ | 100 | 36 | no growth | no growth | - |
| H16 | 2.2 | Co-P\|CoP$_i$-CC | 100 | 36 | 36±8% | 6.4±1.4% | - |
| H16 | 2.2 | Co-P\|CoP$_i$-CC | 1000 | 36 | 30±6% | 5.4±1.1% | - |
| BC4[e] | 2.2 | Co-P\|CoP$_i$-CC | 100 | 36 | 38±11% | 6.9±1.9% | - |
| H16 | 2.2 | Co-P\|CoP$_i$-CC | 100 | 36 | pureCO$_2$:[f] 54±4% / Air:[f] 20±3% | 9.7±0.8% / 3.6±0.5% | - |
| H16 | 2.0 | Co-P\|CoP$_i$-CC | 1000 | 36 | 47±2% | 8.5±0.3% | - |
| BC4[e] | 2.0 | Co-P\|CoP$_i$-CC | 100 | 36 | 42±11% | 7.5±2.0% | - |
| H16 | 1.8 | Co-P\|CoP$_i$-CC | 100 | 36 | no growth | no growth | - |
| H16 | 1.8 | Co-P\|CoP$_i$-CC | 100 | 108 | 28±9% | 5.1±1.6% | - |
| H16[g] | 2.0 | Co-P\|CoP$_i$-CC | 100 | 36 | Biomass: 7±2%[h] / PHB: 36±3%[j] / 42±2%[j] | 1.3±0.4%[h] / 6.4±0.5%[j] / 7.6±0.3%[j] | 701±66[i] |
| Re2133-pEG12 | 2.0 | Co-P\|CoP$_i$-CC | 100 | 36 | Biomass: 13±4% / C$_3$: 31±4%[k] / 39±2%[j,k] | 2.3±0.8% / 5.6±0.8%[k] / 7.1±0.3%[j,k] | 584±53[l] |
| Re2410-pJL26 | 2.0 | Co-P\|CoP$_i$-CC | 100 | 36 | biomass: 13±4% | 2.3±0.6% | 231±44[m] |

Fig. 2

CARBON FIXATION SYSTEMS AND METHODS

This Application is a Divisional of patent application Ser. No. 15/758,843, filed Mar. 9, 2018, which is a national stage filing under 35 U.S.C. 371 of International Patent Application Serial No. PCT/US2016/051621, filed Sep. 14, 2016, which claims the benefit of Provisional Application Ser. No. 62/218,131, filed Sep. 14, 2015. The entire contents of each of which are incorporated herein by reference in their entirety.

GOVERNMENT FUNDING

This invention was made with government support under N00014-11-1-0725 awarded by the Office of Naval Research and under FA9550-09-1-0689 awarded by The Air Force Office of Scientific Research. The government has certain rights in the invention.

FIELD

Disclosed embodiments are related to carbon fixation systems and methods.

BACKGROUND

Sunlight and its renewable counterparts are abundant energy sources that may be harnessed to further sustainable production of materials. For example, photosynthetic organisms harness solar radiation to synthesize energy-rich organic molecules from water and $CO_2$. However, numerous energy conversion bottlenecks exist in natural systems that limit the overall efficiency of photosynthesis. Specifically, most plants do not exceed 1% conversion efficiencies and microalgae grown in bioreactors do not exceed 3% conversion efficiencies. However, conversion efficiencies of 4% for plants and 5%-7% for microalgae present in bubble bioreactors may be achieved in the rapid (short term) growth phase, but not over longer periods. Additionally, although it is possible for artificial photosynthetic solar-to-fuels cycles to have higher intrinsic efficiencies, they typically terminate at hydrogen production, with no process included to complete the cycle by carbon-fixation to create materials with higher energy densities.

SUMMARY

In one embodiment, a method includes: splitting water in a solution containing a chemolithoautotrophic bacteria to form hydrogen ($H_2$) and oxygen ($O_2$) in the solution; providing carbon dioxide ($CO_2$) in the solution; and limiting bioavailable nitrogen in the solution to below a threshold to cause the chemolitoautrophic bacteria to produce a product.

In another embodiment, a system includes a reactor chamber with a solution contained therein. The solution includes hydrogen ($H_2$), carbon dioxide ($CO_2$), bioavailable nitrogen, and a chemolithoautotrophic bacteria. The system also includes a pair of electrodes that split water contained within the solution to produce the hydrogen. A concentration of the bioavailable nitrogen in the solution is below a threshold nitrogen concentration to cause the chemolitoautrophic bacteria to produce a product.

In yet another embodiment, a method includes: splitting water using a cathode including a cobalt-phosphorus alloy and an anode including cobalt phosphate in a solution containing a chemolithoautotrophic bacteria to form hydrogen ($H_2$) and oxygen ($O_2$) in the solution; providing carbon dioxide ($CO_2$) in the solution; and limiting bioavailable nitrogen in the solution to below a threshold to cause the chemolitoautrophic bacteria to produce a product.

In yet another embodiment, a system includes a reactor chamber with a solution contained therein. The solution may include hydrogen ($H_2$), carbon dioxide ($CO_2$), bioavailable nitrogen, and a chemolithoautotrophic bacteria. The system also includes a pair of electrodes that split water contained within the solution to form the hydrogen. The pair of electrodes include a cathode including a cobalt-phosphorus alloy and an anode including cobalt phosphate. A concentration of the bioavailable nitrogen in the solution is below a threshold nitrogen concentration to cause the chemolitoautrophic bacteria to produce a product.

In yet another embodiment, a chemolithoautotrophic bacterium is resistant to reactive oxygen species.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 2 is a table detailing experimental results for different production conditions;

DETAILED DESCRIPTION

Figure 1A:
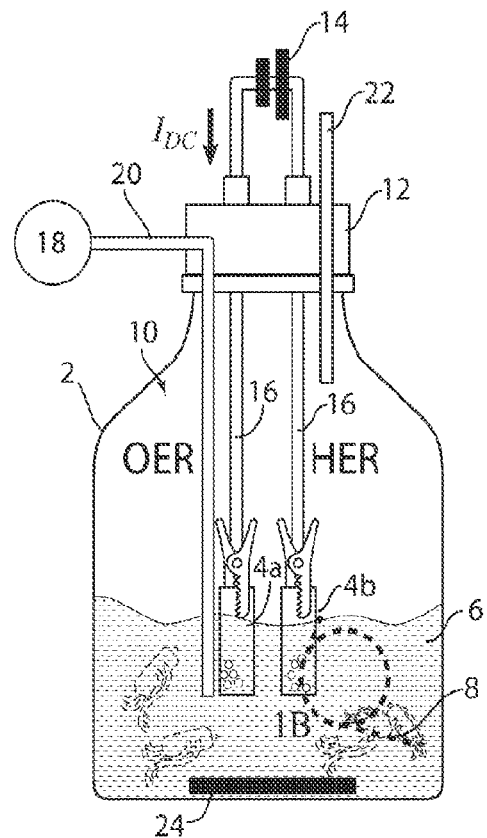
FIG. 1A is a schematic representation of a reactor.

The inventors have recognized that it may be desirable to operate bioreactors for either the production of materials and/or energy storage purposes with higher efficiencies than have been achieved in the past. Additionally, the inventors have recognized that it may be desirable in some instances to enable sustained production of a desired product at higher conversion efficiencies than are achieved in typical reactors. In view of the above, the Inventors have recognized the benefits associated with a reactor including $H_2$-oxidizing autotrophic microorganisms as well as electrodes that split water within a solution in the reactor to generate hydrogen or reducing equivalents within the reactor itself that is then used by the microorganisms to perform carbon fixation to produce a desired product.

In one embodiment, a system includes a reactor chamber containing a solution. The solution may include hydrogen ($H_2$), carbon dioxide ($CO_2$), bioavailable nitrogen, and a bacteria. Gasses such as one or more of hydrogen ($H_2$), carbon dioxide ($CO_2$), nitrogen ($N_2$), and oxygen ($O_2$) may also be located within a headspace of the reactor chamber, though embodiments in which a reactor does not include a headspace such as in a flow through reactor are also contemplated. The system may also include a pair of electrodes immersed in the solution. The electrodes are configured to apply a voltage potential to, and pass a current through, the solution to split water contained within the solution to form at least hydrogen ($H_2$) and oxygen ($O_2$) gasses in the solution. These gases may then become dissolved in the solution. During use, a concentration of the bioavailable nitrogen in the solution may be maintained below a threshold nitrogen concentration that causes the bacteria to produce a desired product. This product may either by excreted from the bacteria and/or stored within the bacteria as the disclosure is not so limited.

Concentrations of the above noted gases both dissolved within a solution, and/or within a headspace above the solution, may be controlled in any number of ways including bubbling gases through the solution, generating the dissolved gases within the solution as noted above (e.g. electrolysis/water splitting), periodically refreshing a composition of gases located within a headspace above the solution, or any other appropriate method of controlling the concentration of dissolved gas within the solution. Additionally, the various methods of controlling concentration may either be operated in a steady-state mode with constant operating parameters, and/or a concentration of one or more of the dissolved gases may be monitored to enable a feedback process to actively change the concentrations, generation rates, or other appropriate parameter to change the concentration of dissolved gases to be within the desired ranges noted herein. Monitoring of the gas concentrations may be done in any appropriate manner including pH monitoring, dissolved oxygen meters, gas chromatography, or any other appropriate method.

As noted above, in one embodiment, the composition of a volume of gas located in a headspace of a reactor may include one or more of carbon dioxide, oxygen, hydrogen, and nitrogen. A concentration of the carbon dioxide may be between 10 volume percent (vol %) and 100 vol %. However, carbon dioxide may also be greater than equal to 0.04 vol % and/or any other appropriate concentration. For example, carbon dioxide may be between or equal to 0.04 vol % and 100 vol %. A concentration of the oxygen may be between 1 vol % and 99 vol % and/or any other appropriate concentration. A concentration of the hydrogen may be greater than or equal to 0.05 vol % and 99%. A concentration of the nitrogen may be between 0 vol % and 99 vol %.

As also noted, in one embodiment, a solution within a reactor chamber may include water as well as one or more of carbon dioxide, oxygen, and hydrogen dissolved within the water. A concentration of the carbon dioxide in the solution may be between 0.04 vol % to saturation within the solution. A concentration of the oxygen in the solution may be between 1 vol % to saturation within the solution. A concentration of the hydrogen in the solution may be between 0.05 vol % to saturation within the solution provided that appropriate concentrations of carbon dioxide and/or oxygen are also present.

As noted previously, and as described further below, production of a desired end product by bacteria located within the solution may be controlled by limiting a concentration of bioavailable nitrogen, such as in the form of ammonia, amino acids, or any other appropriate source of nitrogen useable by the bacteria within the solution to below a threshold nitrogen concentration. However, and without wishing to be bound by theory, the concentration threshold may be different for different bacteria and/or for different concentrations of bacteria. For example, a solution containing enough ammonia to support a Ralstonia eutropha population up to an optical density (OD) of 2.3 produces product at molar concentrations less than or equal to 0.03 M while a population with an OD of 0.7 produces product at molar concentrations less than or equal to 0.9 mM. Accordingly, higher optical densities may be correlated with producing product at higher nitrogen concentrations while lower optical densities may be correlated with producing product at lower nitrogen concentrations. Further, bacteria may be used to produce product by simply placing them in solutions containing no nitrogen. In view of the above, an optical density of bacteria within a solution may be between or equal to 0.1 and 12, 0.7 and 12, or any other appropriate concentration including concentrations both larger and smaller than those noted above. Additionally, a concentration of nitrogen within the solution may be between or equal to 0 and 0.2 molar, 0.0001 and 0.1 molar, 0.0001 and 0.05 molar, 0.0001 and 0.03 molar, or any other appropriate composition including compositions greater and less than the ranges noted above.

While particular gasses and compositions have been detailed above, it should be understood that the gasses located with a headspace of a reactor as well as a solution within the reactor may include compositions and/or concentrations as the disclosure is not limited in this fashion.

Bacteria used in the systems and methods disclosed herein may be selected so that the bacteria both oxidize hydrogen as well as consume carbon dioxide. Accordingly, in some embodiments, the bacteria may include an enzyme capable of metabolizing hydrogen as an energy source such as with hydrogenase enzymes. Additionally, the bacteria may include one or more enzymes capable of performing carbon fixation such as Ribulose-1,5-bisphosphate carboxylase/oxygenase (RuBisCO). One possible class of bacteria that may be used in the systems and methods described herein to produce a product include, but are not limited to, chemolithoautotrophs. Additionally, appropriate chemolithoautotrophs may include any one or more of *Ralstonia eutropha* (*R. eutropha*) as well as *Alcaligenes paradoxs* I360 bacteria, *Alcaligenes paradoxs* 12/X bacteria, *Nocardia opaca* bacteria, *Nocardia autotrophica* bacteria, *Paracoccus denitrificans* bacteria, *Pseudomonas facilis* bacteria, *Arthrobacter* species 11X bacteria, *Xanthobacter autotrophicus* bacteria, *Azospirillum lipferum* bacteria, *Derxia Gummosa* bacteria, *Rhizobium japonicum* bacteria, *Microcyclus aquaticus* bacteria, *Microcyclus ebruneus* bacteria, *Renobacter vacuolatum* bacteria, and any other appropriate bacteria.

Depending on the particular product that it is desired to make, a bacteria may either naturally include a production pathway, or may be appropriately engineered, to include a production pathway to produce any number of different products when placed under the appropriate growth conditions. Appropriate products include, but are not limited to: short, medium, and long chain alcohols including for example one or more of isopropanol ($C_3$ alcohol), isobutanol ($C_4$ alcohol), 3-methyl-1-butanol ($C_5$ alcohol), or any other appropriate alcohol; short, medium, and long chain fatty acids; short, medium, and long chain alkanes; polymers such as polyhydroxyalkanoates including poly(3-hydroxybutyrate) (PHB); amino acids, and/or any other appropriate product as the disclosure is not so limited.

FIG. 1A shows a schematic of one embodiment of a system including one or more reactor chambers. In the depicted embodiment, a single-chamber reactor 2 houses one or more pairs of electrodes including an anode 4a and a cathode 4b immersed in a water based solution 6. Bacteria 8 are also included in the solution. A headspace 10 corresponding to a volume of gas that is isolated from an exterior environment is located above the solution within the reactor chamber. The gas volume may correspond to any appropriate composition including, but not limited to, carbon dioxide, nitrogen, hydrogen, oxygen, and any other appropriate gases as the disclosure is not so limited. Additionally, as detailed further below, the various gases may be present in any appropriate concentration as detailed previously. However, it should be understood that embodiments in which a reactor chamber is exposed to an external atmosphere that may either be a controlled composition and/or a normal atmosphere are also contemplated. The system may also include one or more temperature regulation devices such as a water bath, temperature controlled ovens, or other appropriate configurations and/or devices to maintain a reactor chamber at any desirable temperature range for bacterial growth.

In embodiments where a reactor chamber interior is isolated from an exterior environment, the system may include one or more seals 12. In the depicted embodiment, the seal corresponds to a cork, stopper, a threaded cap, a latched lid, or any other appropriate structure that seals an outlet from an interior of the reactor chamber. In this particular embodiment, a power source 14 is electrically connected to the anode and cathode via two or more electrical leads 16 that pass through one or more pass throughs in the seal to apply a potential to and pass a current $I_{DC}$ to split water within the solution into hydrogen and oxygen through an oxygen evolution reaction (OER) at the anode and a hydrogen evolution reaction (HER) at the cathode. While the leads have been depicted as passing through the seal, it should be understood that embodiments in which the leads pass through a different portion of the system, such as a wall of the reactor chamber, are also contemplated as the disclosure is so limited.

Depending on the particular embodiment, the above-described power source may correspond to any appropriate source of electrical current that is applied to the electrodes. However, in at least one embodiment, the power source may correspond to a renewable source of energy such as a solar cell, wind turbine, or any other appropriate source of current though embodiments in which a non-renewable energy source, such as a generator, battery, grid power, or other power source is used are also contemplated. In either case, a current from the power source is passed through the electrodes and solution to evolve hydrogen and oxygen. The current may be controlled to produce hydrogen and/or oxygen at a desired rate of production as noted above.

In some embodiments, the electrodes may be coated with, or formed from, a water splitting catalyst to further facilitate water splitting and/or reduce the voltage applied to the solution. In some embodiments, the catalysts may be coated onto an electrode substrate including, for example, carbon fabrics, porous carbon foams, porous metal foams, metal fabrics, solid electrodes, and/or any other appropriate geometry or material as the disclosure is not so limited. In another embodiment, the electrodes may simply be made from a desired catalyst material. Several appropriate materials for use as catalysts include, but are not limited to, one or more of a cobalt-phosphorus (Co—P) alloy, cobalt phosphate ($CoP_i$), cobalt oxide, cobalt hydroxide, cobalt oxyhydroxide, a NiMoZn alloy, or any other appropriate material. As noted further below, certain catalysts offer additional benefits as well. For example, in one specific embodiment, the electrodes may correspond to a cathode including a cobalt-phosphorus alloy and an anode including cobalt phosphate, which may help to reduce the presence of reactive oxygen species and/or metal ions within a solution. A composition of the $CoP_i$ coating and/or electrode may include phosphorous compositions between or equal to 0 weight percent (wt %) and 50 wt %. Additionally, the Co—P alloy may include between 80 wt % and 99 wt % Co as well as 1 wt % and 20 wt % P. However, embodiments in which different element concentrations are used and/or other types of catalysts and/or electrodes are used are also contemplated as the disclosure is not so limited. For example, stainless steel, platinum, and/or other types of electrodes may be used.

As also shown in FIG. 1, in some embodiments, it may be desirable to either continuously, or periodically, bubble, i.e. sparge or flush, one or more gases through a solution 6 and/or to refresh a composition of gases located within a head space 10 of the reactor chamber 2 above a surface of the solution. In such an embodiment, a gas source 18 may be in fluid communication with one or more gas inlets 20 that pass through either a seal 12 and/or another portion of the reactor chamber 2 such as a side wall to place the gas source in fluid communication with an interior of the reactor chamber. Additionally, in some embodiments, one or more inlets discharge a flow of gas into the solution so that the gas will bubble through the solution. However, embodiments in which the one or more gas inlets discharge a flow of gas into the headspace of the reactor chamber instead are also contemplated as the disclosure is not so limited. Additionally, one or more corresponding gas outlets 22 may be formed in a seal and/or another portion of the reactor chamber to permit a flow of gas to flow from an interior to an exterior of the reactor chamber. It should be noted that gas inlets and outlets may correspond to any appropriate structure including, but not limited to, tubes, pipes, flow passages, ports in direct fluid communication with the reactor chamber interior, or any other appropriate structure.

Gas sources may correspond to any appropriate gas source capable of providing a pressurized flow of gas to the chamber through the inlet including, for example, one or more pressurized gas cylinders. While a gas source may include any appropriate composition of one or more gasses, in one embodiment, a gas source may provide one or more of hydrogen, nitrogen, carbon dioxide, and oxygen. The flow of gas provided by the gas source may have a composition equivalent to the range of gas compositions described above for the gas composition with a headspace of the reactor chamber. Further, in some embodiments, the gas source may simply be a source of carbon dioxide. Of course embodiments in which a different mix of gases, other including different gases and/or different concentrations than those noted above, is bubbled through a solution or otherwise input into a reactor chamber are also contemplated as the disclosure is not so limited. Additionally, the gas source may be used to help maintain operation of a reactor at, below, and/or above atmospheric pressure as the disclosure is not limited to any particular pressure range.

The above noted one or more gas inlets and outlets may also include one or more valves located along a flow path between the gas source and an exterior end of the one or more outlets. These valves may include for example, manually operated valves, pneumatically or hydraulically actuated valves, unidirectional valves (i.e. check valves) may also be incorporated in the one or more inlets and/or outlets to selectively prevent the flow of gases into or out of the reactor either entirely or in the upstream direction into the chamber and/or towards the gas source.

While the use of inlet and/or outlet gas passages have been described above, embodiments in which there are no inlet and/or outlets for gasses are present are also contemplated. For example, in one embodiment, a system including a sealable reactor may simply be flushed with appropriate gasses prior to being sealed. The system may then be flushed with an appropriate composition of gasses at periodic intervals to refresh the desired gas composition in the solution and/or headspace prior to resealing the reactor chamber. Alternatively, the head space may be sized to contain a gas volume sufficient for use during an entire production run.

In instances where electrodes are run at high enough rates and/or for sufficient durations, concentration may be formed within a solution in a reactor chamber. Accordingly, it may be desirable to either prevent and/or mitigate the presence of concentration gradients in the solution. Therefore, in some embodiments, a system may include a mixer such as a stir bar 24 illustrated in FIG. 1A. Alternatively, a shaker table, and/or any other way of inducing motion in the solution to reduce the presence of concentration gradients may also be used as the disclosure is not so limited.

While the above embodiment has been directed to an isolated reactor chamber, embodiments in which a flow-through reaction chamber with two or more corresponding electrodes immersed in a solution that is flowed through the reaction chamber and past the electrodes are also contemplated. For example, one possible embodiment, one or more corresponding electrodes may be suspended within a solution flowing through a chamber, tube, passage, or other structure. Similar to the above embodiment, the electrodes are electrically coupled with a corresponding power source to perform water splitting as the solution flows past the electrodes. Such a system may either be a single pass flow through system and/or the solution may be continuously flowed passed the electrodes in a continuous loop though other configurations are also contemplated as well.

Figure 1B:
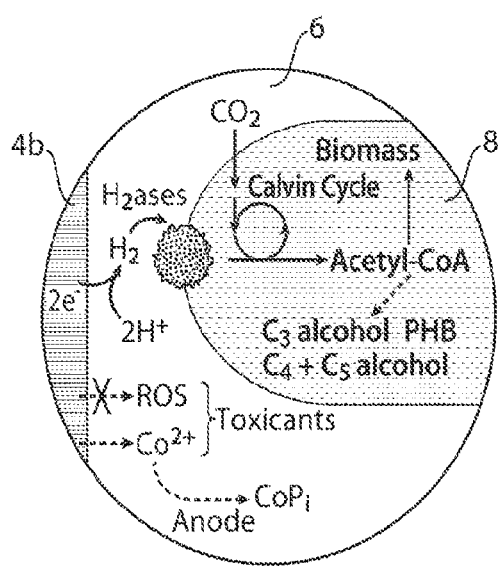
FIG. 1B is a schematic representation of the production of one or more products within the reactor of FIG. 1A.

Without wishing to be bound by theory, FIG. 1B illustrates one possible pathway for a system to produce one or more desired products. In the depicted embodiment, the hydrogen evolution reaction occurs at the cathode $4b$. During the reaction at the cathode, two hydrogen ions ($H^+$) are combined with two electrons to form hydrogen gas $H_2$ that dissolves within the solution 6 along with carbon dioxide ($CO_2$), which dissolved in the solution as well. At the same time various toxicants such as reactive oxygen species (ROS) including, for example, hydrogen peroxide ($H_2O_2$), superoxides ($O_2 \cdot^-$), and/or hydroxyl radical (HO.) species as well as metallic ions may be generated at the cathode. For example, $Co^{2+}$ ions may be dissolved into solution when a cobalt based cathode is used. As described further below, in some embodiments, the use of certain catalysts may help to reduce the production of ROS and the metallic ions leached into the solution may be deposited onto the anode using one or more elements located within the solution to form compounds such as a cobalt phosphate.

As also illustrated in FIG. 1B, once hydrogen and carbon dioxide are provided within a solution, bacteria 8 present within the solution may be used to transform these compounds into useful products. For example, in one embodiment, the bacteria uses hydrogenase to metabolize the dissolved hydrogen gas and one or more appropriate enzymes, such as RuBisCO or other appropriate enzyme, to provide a carbon fixation pathway. This may include absorbing the carbon dioxide and forming Acetyl-CoA through the Calvin cycle as shown in the figure. Further, depending on the concentration of nitrogen within the solution, the bacteria may either form biomass or one or more desired products. For instance, if a concentration of nitrogen within the solution is below a predetermined nitrogen concentration threshold, the bacteria may form one or more products such as the C3, C4, and/or C5 alcohols, PHB, and/or combinations of the above depicted in the figure.

Depending on the embodiment, a solution placed in the chamber of a reactor may include water with one or more additional solvents, compounds, and/or additives. For example, the solution may include: inorganic salts such as phosphates including sodium phosphates and potassium phosphates; trace metal supplements such as iron, nickel, manganese, zinc, copper, and molybdenum; or any other appropriate component in addition to the dissolved gasses noted above. In one such embodiment, a phosphate may have a concentration between 9 and 90 mM, 9 and 72 mM, 9 and 50 mM, or any other appropriate concentration. In a particular embodiment, a water based solution may include one or more of the following in the listed concentrations: 12 mM to 123 mM of $Na_2HPO_4$, 11 mM to 33 mM of $KH_2PO_4$, 1.25 mM to 15 mM of $(NH_4)_2SO_4$, 0.16 mM to 0.64 mM of $MgSO_4$, 2.4 µM to 5.8 µM of $CaSO_4$, 1 µM to 4 µM of $NiSO_4$, 0.81 µM to 3.25 µM molar concentration of Ferric Citrate, 60 mM to 240 mM molar concentration of $NaHCO_3$.

As noted above in regards to the discussion of FIG. 1B, reactive oxygen species (ROS) as well as metallic ions may be formed and/or dissolved into a solution during the hydrogen evolution reaction at the cathode. However, ROS and larger concentrations of the metallic ions within the solution may be detrimental to cell growth above certain concentrations. It is noted that the use of continuous hydrogen production within a reactor to form hydrogen for conversion into one or more desired products has been hampered by the production of these ROS and metallic ion concentrations because the bacteria used to form the desired products tend to be sensitive to these compounds and ions limiting the growth of, and above certain concentrations, killing the bacteria. Therefore, in some embodiments, it may be desirable to apply voltages, use electrodes that produce less ROS, remove and/or prevent the dissolution of metallic ions from the electrodes, and/or use bacteria that are resistant to the presence of these toxicants as detailed further below.

As noted above, it may be desirable to select one or more catalysts for use as the electrodes that produce fewer reactive oxygen species (ROS) during use. Specifically, a biocompatible catalyst system that is not toxic to the bacterium and lowers the overpotential for water splitting may be used in some embodiments. One such example of a catalyst includes a ROS-resistant cobalt-phosphorus (Co—P) alloy cathode. This cathode may be combined with a cobalt phosphate ($CoP_i$) anode. This catalyst pair has the added benefit of the anode being self-healing. In other words, the catalyst pair helps to remove metallic $Co^{2+}$ ions present with a solution in a reactor. Without wishing to be bound by theory, the electrode pair works in concert to remove extracted metal ions from the cathode by depositing them onto the anode which may help to maintain extraneous cobalt ions at relatively low concentrations within solution and to deliver a low applied electrical potential to split water to generate $H_2$. Without wishing to be bound by theory, it is believed that during electrolysis of the water, phosphorus and/or cobalt is extracted from the electrodes. The reduction potential of leached cobalt is such that formation of cobalt phosphate using phosphate available in the solution is energetically favored. Cobalt phosphate formed in solution then deposits onto the anode at a rate linearly proportional to free $Co^{2+}$, providing a self-healing process for the electrodes. In view of the above, the cobalt-phosphorus (Co—P) alloy and cobalt phosphate ($CoP_i$) catalysts may be used to help mitigate the presence of both ROS and metal ions within the solution to help promote growth of bacteria within the reactor chamber.

It should be understood that any appropriate voltage may be applied to a pair of electrodes immersed in a solution to split water into hydrogen and oxygen. However, in some embodiments, the applied voltage may be limited to fall between upper and lower voltage thresholds. For example, the self-healing properties of a cobalt phosphate and cobalt phosphorous based alloy electrode pair may function at voltage potentials greater than about 1.42 V. Additionally, the thermodynamic minimum potential for splitting water is about 1.23 V. Therefore, depending on the particular embodiment, the voltage applied to the electrodes may be greater than or equal to about 1.23 V, 1.42 V, 1.5 V, 2 V, 2.2 V, 2.4 V, or any other appropriate voltage. Additionally, the applied voltage may be less than or equal to about 10 V, 5 V, 4 V, 3 V, 2.9 V, 2.8 V, 2.7 V, 2.6 V, 2.5 V, or any other appropriate voltage. Combinations of the above noted voltage ranges are contemplated including, for example, a voltage applied to a pair of electrodes may be between 1.23 V and 10 V, 1.42 V and 5 V, 2 V and 3 V, 2.3 V and 2.7 V as well as other appropriate ranges. Additionally, it should be understood that voltages both greater than and less than those noted above, as well as different combinations of the above ranges, are also contemplated as the disclosure is not so limited. In addition to the applied voltages, any appropriate current may be passed through the electrodes to perform water splitting which will depend on the desired rate of hydrogen generation for a given volume of a reactor being used. For example, in some embodiments, a current used to split water may be controlled to generate hydrogen at a rate substantially equal to a rate of hydrogen consumption by bacteria in the solution. However, embodiments in which hydrogen is produced at rates both greater than or less than consumption by the bacteria are also contemplated.

In addition to using catalysts, controlling the solution pH, and applying appropriate driving potentials, and/or controlling any other appropriate parameter to reduce the presence of reactive oxygen species (ROS) within the solution in a reaction chamber, it may also be desirable to use bacteria that are resistant to the presence of ROS and/or metallic ions present within the solution as noted previously. Specifically, a chemolithautotrophic bacterium that is resistant to reactive oxygen species may be used. Further, in some embodiments a *R. eutropha* bacteria that is resistant to ROS as compared to a wild-type H16 *R. eutropha* may be used. Table I below details several genetic polymorphisms found between the wild-type H16 *R. eutropha* and a ROS-tolerant BC4 strain that was purposefully evolved during the experiments detailed below. Mutations of the BC4 strain relative to the wild type bacteria are detailed further below.

Two single nucleotide polymorphisms and two deletion events were observed. Without wishing to be bound by theory, the large deletion from aciC1 may indicate a decrease in overall membrane permeability, possibly affecting superoxide entry to the cell resulting in the observed ROS resistance. The genome sequences are accessible at the NCBI SRA database under the accession number SRP073266 and specific mutations of the BC4 strain are listed below in Table 1. The standard genome sequence for the wild-type H16 *R. eutropha* is also accessible at the RCSB Protein Data Bank under accession number AM260479 which the following mutations may also be referenced to.

TABLE I

| Mutation | Position | Annotation | Gene | Description |
|---|---|---|---|---|
| G → T | 611,894 | R133R | acrC1 | cation/multidrug efflux system outer membrane protein |
| Δ45 bp | 611,905 | 344-388 of 1494 nt | acrC1 | cation/multidrug efflux system outer membrane protein |
| G → A | 2,563,281 | intergenic, (−1/+210) | Hfq and H16_A2360 | uncharacterized host factor I protein/GTP-binding protein |
| Δ15 bp | 241,880 | 363-377 of 957 nt | H16_B0214 | transcriptional regulator, LysR-Family |

In reference to the above table, an *R. eutropha* bacteria may include at least one to four mutations selected from the mutations noted above in Table 1 and may be selected in any combination. These specific mutations are listed below in more detail with mutations noted relative to the wild type *R. eutropha* bolded and underlined within the sequences given below.

The first noted mutation may correspond to the sequence listed below ranging from position 611790-611998 for *Ralstonia eutropha* H16 chromosome 1.

(SEQ ID NO: 1)
GCCTCGCTGCTTTCCACCTGGCGCCGCACGCGGCCCCAGACGTCGA

TTTCCCAGGTTGCGCCCAGGGTCGCGCTCTGCCCGTTGAGCGTGCTGCCG

CTGGCGCCGCGCGCGCGAGGCGCCGGCCTGTGCGTCGACGGTCGGAA

GAAGCCGGCGCGCGCGGCCTGCAGCGACGCCACCGCCTGGCGGTACTGCG

CCTCGGCGGCCTT

The second noted mutation may correspond to the sequence listed below ranging from position 611905-613399 for *Ralstonia eutropha* H16 chromosome 1.

(SEQ ID NO: 2)
AGGCGCCGGCCTGTGCGTCGACGGTCGGGAAGAAGCCGGCGCGCG

CGGCCTGCAGCGACGCCACCGCCTGGCGGTACTGCGCCTCGGCGGCCTTG

ATGTTCTGGTTCGAGATCTGCACCTCGGACATCAGCGCGTCGAGCTGCGC

ATCGCCGAACACGGTCCACCAGTCGGCGCGTGCCAGCGCATCCTGCGGCT

CGGCGGGCTTCCAGTCGCCGGTCCAGGCGGGGTGGCGGCATCGGCTTCC

TTGAAGGATGCGGAAACCGGCGCGTCGGGGCGCTGGTAGTCGGGGCCGAC

GGCGCAGCCGGCCAGCAGCAGCGCGCAGGCCAGCGACACCGGCAGGGCAT

GGGTCAGGAGGCGGGAAAGAACTGTCATGTCGAGTCTTCGCAAATCTAGA

CGGCGGCCGGCTGGTCAGGCGTGCCGGCACCACGGCGGCGCTGGCGCCAG

GCCTTGACCTTCAGGCGCCAGCGGTCCAGCGTCAGGTAGACCACCGGCGT

GGTGTACAGCGTCAGCAGCTGGCTTACCACCAGTCCGCCGACAATGGAGA

TGCCCAGCGGCGCGCGCAGTTCGGCGCCGTCGCCGCGGCCGATTGCCAGC

GGCACCGCGCCCAGCAGCGCGGCCATGGTGGTCATCAGGATCGGGCGGAA

GCGCAGCAGGCAGGCGCGGTAGATCGCGTCGCGCGGCGACAGGCCATCGC

GCCGTTCGGCATCGATGGCGAAGTCGATCATCATGATCGCGTTCTTTTTC

ACGATGCCGATCAGCAGGATCACGCCGATCAGCGCGATGATGCTGAAGTC

GGTCTTCGATGCCAGCAGCGCCAGCAGCGCGCCCACGCCGGCGGAGGGCA

GCGTCGACAGGATCGTCAGCGGATGCACATAGCTTTCATACAGCACGCCC

AGCACGATGTAGATCGTGATCAGCGCCGCCAGGATCAGGATCGGCTGACT

CTTGAGCGAATCCTGGAACGCCTTGGCGCCGCCCTGGAAGTTGGCGCGCA

GCGTCTCCGGCACGCCGATGCGCGCCATCTCGCGCGTGATCGCGTCGGTC

GCCTGCGACAGCGAAGTGCCCTCGGCCAGGTTGAACGAGATCGTCGAGGC

CGCGAACTGGCCCTGGTGGTTCACGCCCAGCGGCGTGCTGGACGGGGTCA

CGCGCGCGAACGCCGCCAGCGGCACGCGGTTGCCGTTGCCGGTGACCACG

TAGATGTCCTTGAGCGCATCGGGCCCTTGCAGGTATTCCTGGCTCAGCTC

CATCACCACGCGGTACTGGTTCAGCGGATGGTAGATGGTGGACACCAGCC

GCTGGCCGAAGGCATCGTTGAGCACCGCATCCACCTGCTGCGCGGTCACG

CCCAGGCGCGAGGCCGCGTCGCGGTCGATGATCACCGAGGTCTGCAGGCC

CTTGTCGTTGGTATCGGTGTCGATATCCTCCAGCCCCTTCAGGTTCGACA

ACGCGGCGCGCACCTTGGGCTCCCACGCGCGCAGCACTTCCAGGTCGTCC

The third noted mutation may correspond to the sequence listed below ranging from position 2563181-2563281 for *Ralstonia eutropha* H16 chromosome 1.

(SEQ ID NO: 3)
GCAGCTTGATGCCATTGACGAGGTAGATGGAAACCGGCACGTGCTC

TTTGCGCAGCGCGTTCAGGAACGGGCCTTGTAGCAGTTGCCCTTTGTTG

CTCATGGCACACTCCAAATTTATAGGTTTAGTGGTGAATGATGGGGATG

GAAATCCCCGGTTCAAGTCAGGCGGCGCAAAAACGCGCCAGAAAAAAGA

TCAAAAAC

The fourth noted mutation may correspond to the sequence listed below ranging from position 241880-242243 for *Ralstonia eutropha* H16 chromosome 1.

(SEQ ID NO: 4)
GAGGATGCCATGTCCGAAGCGCCTGTCCTTGCCCCCTCGACCTCAA

CCCAGCCGCCCGCCGCCGGCCAGCTCAACCTGATCCGCCCGCAGCCATAT

GCCGACTGGGCGCCGCAGGTCACGGCCGAAGAACGCGCCACGCTGCGCCG

CGAGCTGGAGCAGGGCGCCGTGCTGTACTTCCCGAACCTGAATTTCCGCT

TCCAGCCGGGCGAAGAGCGCTTCCTTGACAGCCGCTATTCCGACGGCAAG

-continued
TCCAAGAACATCAACCTGCGCGCCGACGACACCGCGGTGCGCGGCGCCCA

GGGCAGTCCGCAGGACCTGGCGGACCTGTACACGCTGATCCGCCGCTACG

CCGACAACAGCGAATTGCTGGTGCGCACGCTGTTCCCTGAATACATCCCG

CACATGACGCGCGCCGGCACCTCGCTGCGGCCCAGCGAGATCGCCGGGCG

CCCGGTCAGCTGGCGCAAGGACGACACCCGCCT

In the above sequences, it should be understood that a bacteria may include changes in one or more base pairs relative to the mutation sequences noted above that still produce the same functionality and/or amino acid within the bacteria. For example, a bacteria may include 95%, 96%, 97%, 98%, 99%, or any other appropriate percentage of the same mutation sequences listed above while still providing the noted enhanced ROS resistance.

As elaborated on in the examples, the systems described herein are capable of undergoing intermittent production. For example, when a driving potential is applied to the electrodes to generate hydrogen, the bacteria produce the desired product. Correspondingly, when the potential is removed and hydrogen is no longer generated, production of the product is ceased once the available hydrogen is consumed and a reduction in overall biomass is observed until the potential is once again applied to the electrodes to generate hydrogen. The system will then resume biomass and/or product formation. Thus, while a system may be run continuously to produce a desired product, in some modes of operation a driving potential may be intermittently applied to the electrodes to intermittently split water to form hydrogen and correspondingly intermittently produce a desired product. A frequency of the intermittently applied potential may be any frequency and may either be uniform or non-uniform as the disclosure is not so limited. This ability to intermittently produce a product may be desirable in applications such as when intermittent renewable energy sources are used to provide the power applied to the electrodes including, but not limited to, intermittent power sources such as solar and wind energy.

EXAMPLES: EXPERIMENTAL SYSTEMS

The solution used during the experiments described herein was prepared according to the following procedure. A first solution was prepared using 940 mL deionized H2O, 6.74 g $Na_2HPO_4\text{-}7H_2O$, 1.5 g $KH_2PO_4$, and 1.0 g $(NH_4)_2SO_4$. A second solution was prepared with 400 mL deionized $H_2O$, 4.0 g $MgSO_4\text{-}7H_2O$, 50 mg $CaSO_4\text{-}2H_2O$ (stirred extensively to dissolve), and 28 mg $NiSO_4\text{-}7H_2O$. A third solution was prepared with 400 mL deionized $H_2O$ and 20 mg Ferric citrate. A fourth solution was prepared using 400 mL deionized $H_2O$ and 10.0 g $NaHCO_3$. Without wishing to be bound by theory, the first, second, and fourth solutions were filtered and sterilized. The third solution was not. The second, third, and fourth solutions where then combined with the first solution and mixed to combine.

The above described media had an overall phosphate salt concentration of 36 mM which may be decreased to about 9 mM before the weakly buffered solution began to deteriorate the carbon cloth anode during use. However, different concentrations may be useable with different anode substrate materials. Additionally, it was found that R. eutropha was capable of tolerating 72 mM phosphate salt (2×) but died at a phosphate salt concentrations greater than or equal to 108 mM (3×) reliably. Though again, different appropriate solution concentrations may be used for different bacteria and/or when used with different solution compositions. At 36 mM phosphate salts, the pH of the solution with under 400 ppm $CO_2$ was 7. R. eutropha media typically range from pH=6-8 but hydrogenase has been shown to operate as low as pH=4.5. At a 100% $CO_2$ headspace at 1 atm, the final pH was about 6.2. Without wishing to be bound by theory, the sodium bicarbonate helped to maintain osmotic pressure and ionic strength. Therefore, a concentration of the sodium bicarbonate was balanced based on the pH.

The cobalt phosphorous alloy and cobalt phosphate catalysts for hydrogen evolution reaction (HER) and oxygen evolution reaction (OER) were created by electrochemical deposition methods with the use of a Gamry Interface 1000 potentiostat. A classic three-electrode setup was applied with a Ag/AgCl, 1 M KCl reference electrode. After depositing the catalysts, the electrodes were rinsed with ample deionized water.

Water splitting and bacterial $CO_2$ fixation took place in a single enclosed chamber filled with $CO_2$ in the headspace similar to the chamber shown in FIG. 1 above. The reported data are based on at least three biological replicates (n≥3). A Gamry Reference 600 potentiostat coupled with an ECM8 electrochemical multiplexer allowed for parallel experiments with 8 individual reactors. The reactors included a 250 mL Duran® GL 45 glass bottle capped with a Duran® GL 45 3-ports (GL 14) connection system. The glass bottles were immersed in a 30° C. water bath. Two of the GL 14 screw cap ports on each reactor served as the feedthroughs for the two water-splitting electrodes, and a third feed through was used as a gas inlet regulated by a quarter-turn valve. For a typical experiment, 100 mL of all-inorganic minimal media solution was added into the reactor and water splitting was performed via a two-electrode system; the electrodes had a 4 $cm^2$ geometric area. The applied potential, $E_{appl}$, was defined as the voltage difference between the working and counter/reference electrodes in a two-electrode configuration; $E_{appl}$ is detailed in the table shown in FIG. 2 for each experiment.

After inoculation with R. eutropha strains (initial $OD_{600}$=0.2), the reactor was purged with $CO_2$ and then sealed. The experiments were stirred at 350 rpm by a triangular stirring rod to facilitate mass transport within the reactors. The bioelectrochemical reactor headspace was sampled daily using Supel™ inert foil gas sampling bags. The electrolyte was also sampled daily to quantify $OD_{600}$ and product titers. After sampling, the reactor headspace was sparged to refill $CO_2$ in the headspace. In the case of $CO_2$ reduction directly from air, the reactor chamber was not isolated to the environment. The gas inlet port was connected to the ambient atmosphere through a 0.2 μm PVDF gas filter and no $CO_2$ gas flow was supplied to the reactor headspace. In this setup, the reactor headspace was in direct exchange with ambient environment through the PVDF filter.

Of course, while isolated batch reactor designs were used in the experiments, the batch reactor design may be modified to a flow-based configuration, in which microbe-containing media would be forced to flow through a chamber where water splitting occurs. As detailed further below, the low level of residual $H_2$ gas measured in the headspace indicates the efficient uptake of $H_2$ and accordingly a small energy loss would be expected under a flow reactor configuration making it a viable design choice.

Real-time monitoring of biomass accumulation was accomplished by measuring the optical density of the 100 mL reactors on a home-built setup at 20 sec time intervals. Specifically, a 650 nm laser pointer (Digi-Key Electronic)

was directed at a photodiode across the 100 mL reactor containing bacteria and water splitting electrodes. Controlled through a customized script in MATLAB, every 20 sec the intensity of incident light after scattering the culture was determined with the help of an operational amplifier (Digi-Key Electronic). A standard curve between the measured light intensity and $OD_{600}$ was established, after measuring the transmitted light from *R. eutropha* cultures of known $OD_{600}$ values.

In some experiments, a 10-fold scale-up experiment was conducted. In these experiments, a similar reactor was used but included a 1000 mL volume reactor. Other than as noted below, the procedure was similar to that employed for experiments using the 100 mL reactor. A Vacu-Quik jar system (Almore International, inc.) was modified with two current feedthroughs for water splitting electrodes and two PEEK tubes as gas inlet/outlet. A Neslab EX-211 constant temperature bath circulated water around the jar to maintain a temperature of 30° C. For optimized temperature homogeneity, the jar and the water circulation was embedded in a thermally insulating layer. The volume of minimal medium solution was 1000 mL, and the size of the electrodes was increased proportionally. During the experiments, the reactor was inoculated with *R. eutropha* ($OD_{600}$=0.05) and grown under $H_2/CO_2$/air overnight. Before $CO_2$ reduction was begun, the initial $OD_{600}$ referenced signal of the bacterial optical density was recorded. The measured signal was typically between 0.15 and 0.20 times the reference $OD_{600}$ signal. The headspace of the reactor was then thoroughly purged with $CO_2$ to remove the residual $H_2$ that remained from the autotrophic growth.

Facilitating $CO_2$ mass transport by pressurization was not observed to be beneficial in the current experiments. However, under some conditions, such as during the use of larger reactors, pressurized reactor operation may be beneficial.

Example: Bacterial Strains and Growth Protocols

Unless noted otherwise, the composition of the minimal medium used was 6.74 g/L $Na_2HPO_4 \cdot 7H_2O$, 1.5 g/L $KH_2PO_4$, 1.0 g/L $(NH_4)_2SO_4$, 80 mg/L $MgSO_4 \cdot 7H_2O$, 1 mg/L $CaSO_4 \cdot 2H_2O$, 0.56 mg/L $NiSO_4 \cdot 7H_2O$, 0.4 mg/L ferric citrate, and 200 mg/L $NaHCO_3$. Because nitrogen (N), phosphorous (P) and sulfur (S) are contributing about 10% (for N) and less than 5% (for P and S) of the total dry cell weight, the requirement of inorganic elements is not limiting the $CO_2$-reduction process under the listed experimental conditions. The constant renewal of "living" biocatalysts does not factor into the consumption of inorganic elements, because new bacteria can recycle the elements released from the expired microbes. This medium composition had a phosphate buffer concentration of 36 mM. To induce nitrogen-limited growth of the bacteria to produce isopropanol and PHB, the $(NH_4)_2SO_4$ concentration was reduced to 0.167 g/L. For experiments with higher salinity, the buffer strength of phosphate was increased by three times: 20.22 g/L $Na_2HPO_4 \cdot 7H_2O$, 4.5 g/L $KH_2PO_4$. This "high salt" medium had a phosphate buffer concentration of 108 mM. All solutions were filter-sterilized prior to use except the ferric citrate component, which was added after the filter sterilization step.

$NaHCO_3$ was also added to the initial media preparation to maintain ionic strength and osmotic pressure. As a conjugate base under equilibrium with $CO_2$ in aqueous solution, bicarbonate can serve as a carbon source for $CO_2$ reduction. *R. eutropha* converts bicarbonate to $CO_2$ through carbonic anhydrase. The prepared media was fully equilibrated before any experiments were conducted.

*R. eutropha* H16 (wild type), Re2133-pEG12, and Re2410-pJL26 strains were obtained from Sinskey laboratory at MIT. Additionally, as detailed below, a ROS-resistant strain (BC4) was isolated that was evolved after 11 consecutive days of exposure to a stainless steel cobalt phosphate water-splitting system with an applied electrode potential of 2.3 V. During the development of this ROS resistant strain, no growth was observed until day 7 when the $OD_{600}$ rose from 0.15 to 1.15 over the next 4 days. Isolated strains were sequenced and mutations were compiled using breseq.

Unless noted otherwise, all of the microbial growth was conducted at 30° C. In general, individual colonies were picked from agar plates and inoculated into rich broth media solutions for overnight growth. Cultures were centrifuged and re-suspended in minimal medium supplemented with gentamicin (10 µg/mL). The cultures were placed in a Vacu-Quick jar filled with $H_2$ (8 mmHg) and $CO_2$ (2 mmHg) with air as balance. At this condition, *R. eutropha* adapted to autotrophic metabolism with $H_2$.

Example: Toxicant Quantification

Abiotic water splitting was performed in the bioelectrochemical reactors described above using minimal medium solution as the electrolyte with a number of electrode combinations. 50 µL of electrolyte was then transferred at a series of time points to a 96-well plate (Corning). The plate was kept on ice, in the dark, for no more than 1 hour prior to measurement. The $H_2O_2$ concentration was assayed using an Amplex Red $H_2O_2$ detection kit (Sigma-Aldrich) by monitoring the absorbance at 555 nm using a BIO-13 Synergy H1m plate reader. The concentration of $H_2O_2$ was quantified by comparing against a standard curve generated from $H_2O_2$ standards ranging from 0 to 40 µM.

The leaching rates of various elements from the electrodes was also measured with inductively coupled plasma mass spectrometry (Thermo Electron, X-Series ICP-MS with collision cell technology, CCT). After running the abiotic water-splitting experiments for 24 hours at constant $E_{appl}$, 0.5 mL of electrolyte was sampled and diluted with 3.5 mL of 2% double distilled nitric acid (Sigma-Aldrich). Samples along with calibration standards were scanned twice for 60 sec each for $^{60}Ni$, $^{59}Co$, and $^{194}Pt$. To demonstrate the "self-healing" effect of $CoP_i$ anode on the metals leached from cathode, experiments were conducted in both one- and two-compartment electrochemical cells. In the single-compartment setup, both the HER cathode and OER anode were immersed in the same reactor. In the two-compartment setup (H-cell), a glass frit junction of fine porosity separated the two chambers and hindered the mass transport of leached metal ions.

The procedure for spot assays was performed by diluting 100 µL of culture grown under different conditions by 1:10 in fresh minimal medium, which was vortexed. Three to four serial 10-fold dilutions were made and 2 µL of each dilution was spotted on rich broth agar plates and allowed to dry. Plates were typically grown for 2 days at 30° C. before imaging. The half maximal inhibitory concentration ($IC_{50}$) was estimated based on the comparison at 1/100 dilution. The areas of colonies at certain conditions were then compared with that of control samples.

Example: $CO_2$ Fixation

Figure 3:
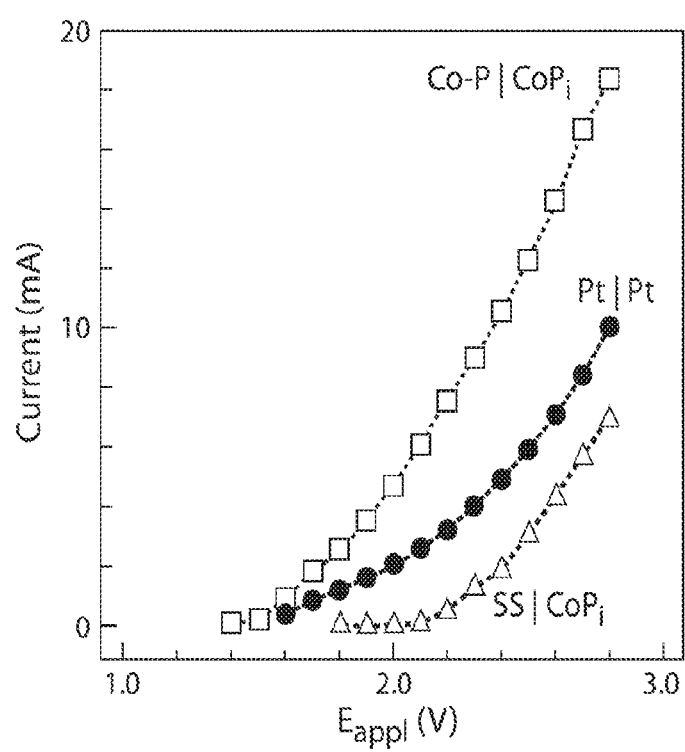
FIG. 3 is a graph of current voltage characteristics of different water splitting catalysts.
Figure 4:
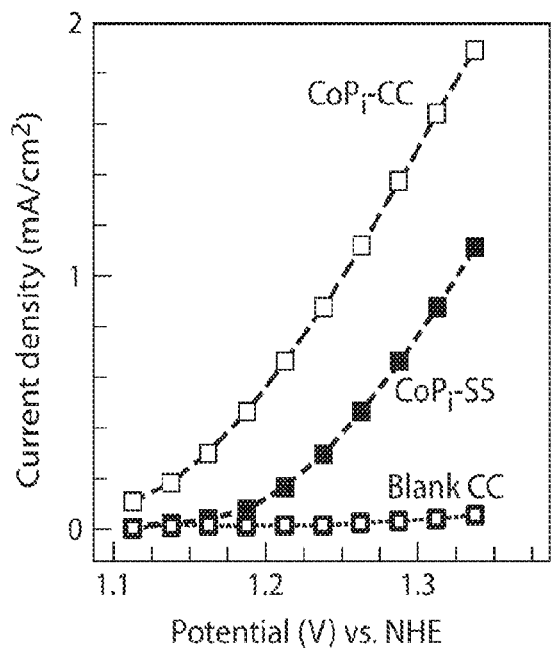
FIG. 4 is a graph of current density versus potential for $CoP_i$ on a carbon cloth versus $CoP_i$ coated on stainless steel and a blank carbon cloth.
Figure 5:
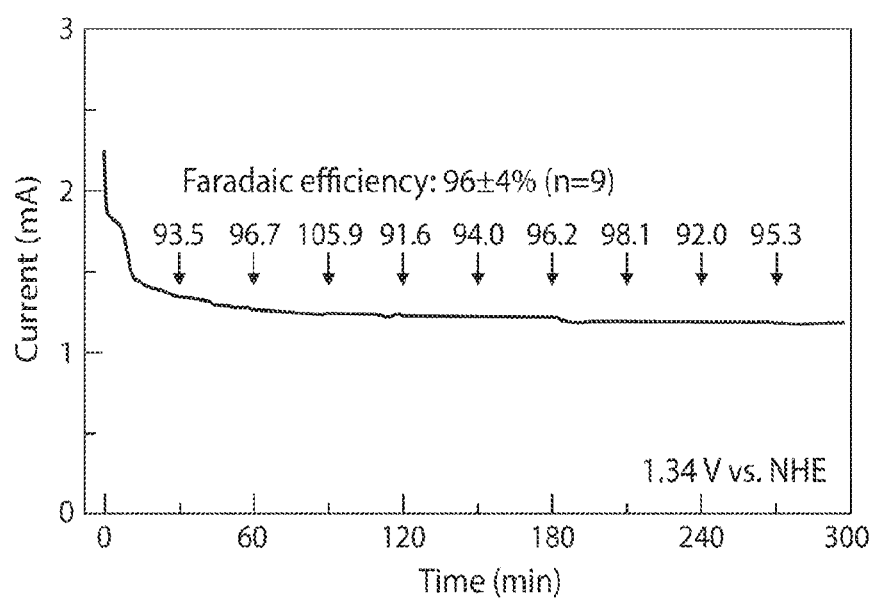
FIG. 5 is a graph of current versus time illustrating the faradaic efficiency of $CoP_i$ coated on a carbon cloth.

Using the biocompatible Co—P|$CoP_i$ water splitting catalysts noted above along with *R. eutropha* resulted in a system capable of performing $CO_2$-fixation using continuous $H_2$ production via water splitting. For these experiments, the $CoP_i$ catalyst was deposited on a high-surface-area carbon cloth as the electrode support. This configuration resulted in relatively high currents as compared to stainless steel paired with a $CoP_i$ electrode and a platinum electrode pair, FIG. 3. As shown in FIGS. 4 and 5, a faradaic efficiency of the electrodes was 96±4%. During use, $CO_2$ reduction proceeded under a constant voltage within the batch reactor similar to the one described above relative to FIG. 1. The batch reactor was half-filled with a solution containing only inorganic salts (mostly phosphate) and trace metal supplements.

Figure 6:
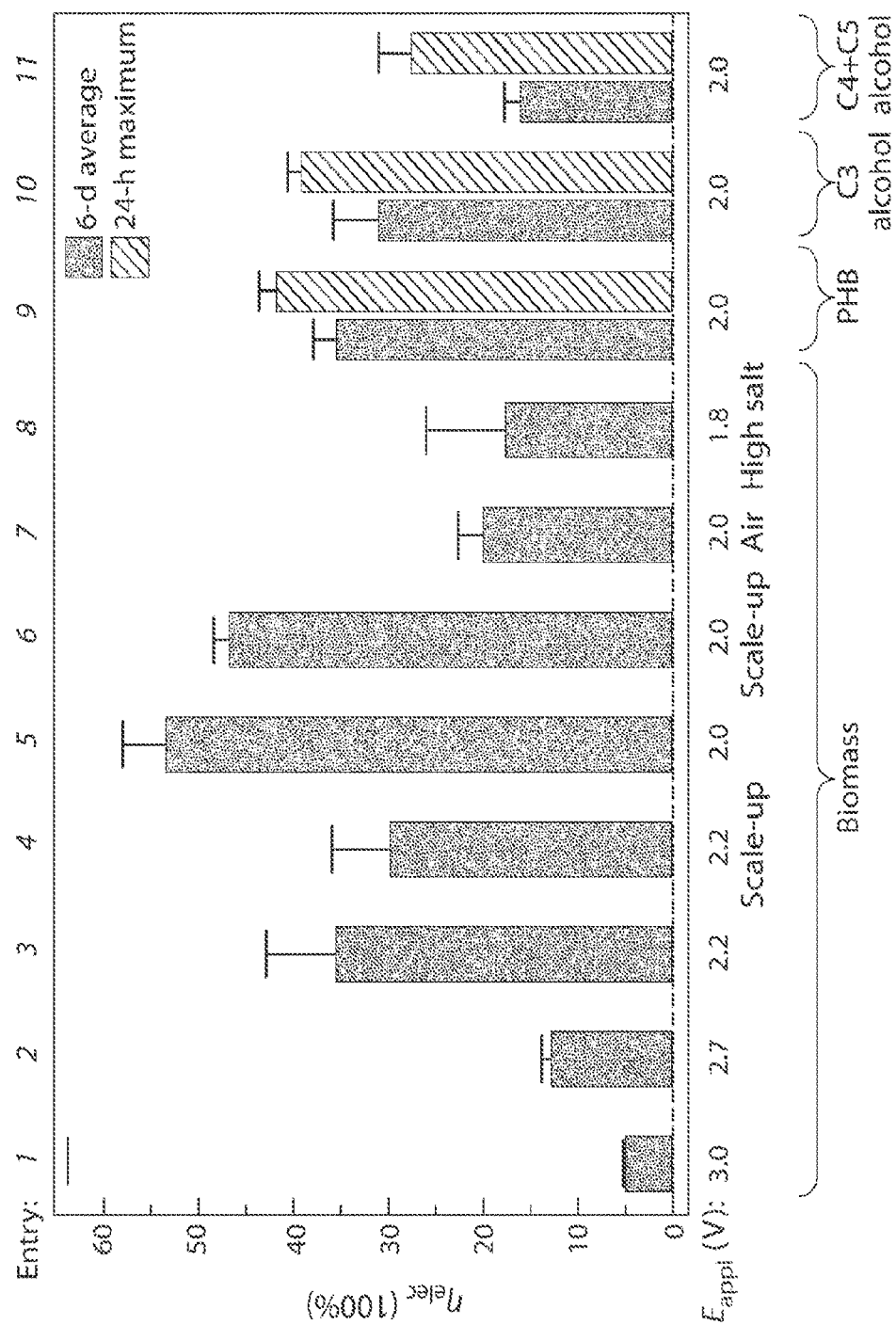
FIG. 6 is a graph of energy efficiencies $\eta_{elec}$ and kinetics for the production of biomass and products at different applied potentials and system configurations with the solid bars indicating averages of 5-6 days and dashed bars indicating 24-hr maximums.
Figure 7:
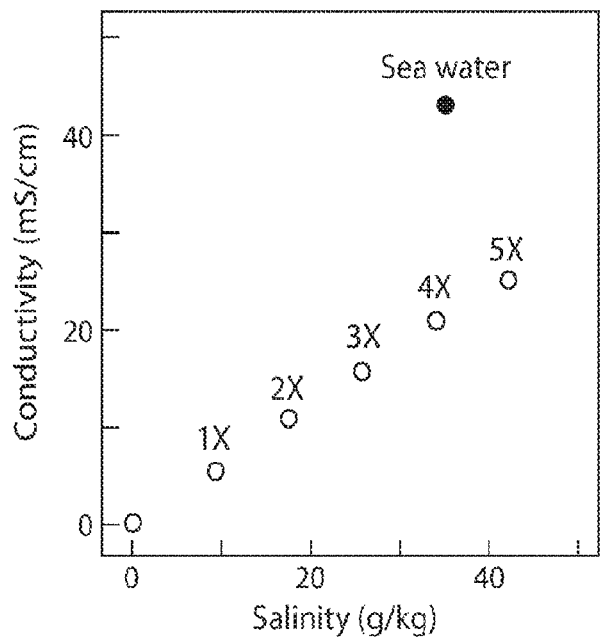
FIG. 7 is a graph of conductivity versus salinity.
Figure 8:
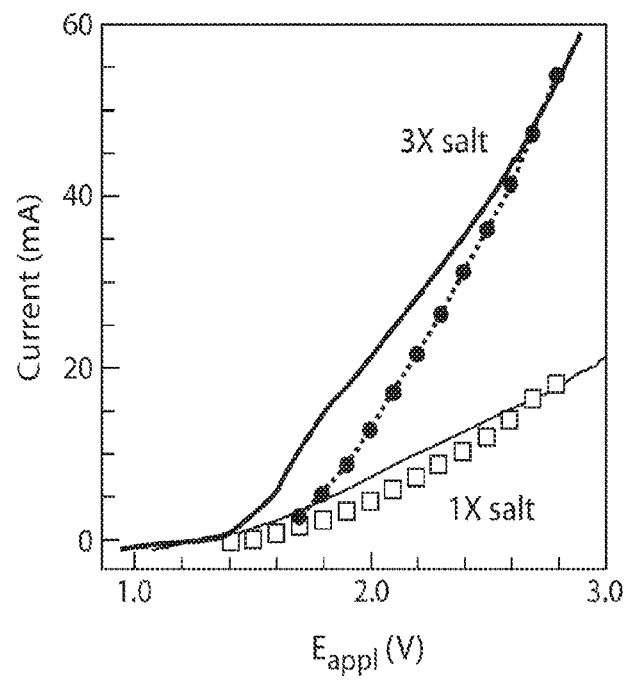
FIG. 8 is a graph of water-splitting currents in solutions of higher salinity.

The table shown in FIG. 2 illustrates the results from multiple experiments including different electrodes, bacterium strains, applied voltages, volumes, and solution compositions. Efficiencies and titers for different $E_{appl}$ and other experimental conditions were averaged over 5-6 days unless specifically noted otherwise in the table. As shown in the table and FIG. 6, using a $CoP_i|Co-P$ electrode pair in combination with *R. eutropha*, the system was able to store over half its input energy as products of $CO_2$-fixation at low $E_{appl}$. Entries 1-3 and 5 show that $\eta_{elec}$ increases with decreasing $E_{appl}$ under 100% $CO_2$ until $E_{appl} < 2.0$ V. Below $E_{appl} = 2.0$ V (Entry 8). A higher salt concentration (108 mM phosphate buffer) was also tried to facilitate mass transport and attendant current, FIGS. 7 and 8. However, higher salt concentrations were found to limit *R. eutropha* metabolism. Thus a concentration of 36 mM phosphate and $E_{appl} = 2.0$ V resulted in an optimal $\eta_{elec}$ for these experiments, though different concentrations with different bacteria, solutions, and/or system configurations may also occur. The highest observed $\eta_{elec}$ achieved for biomass production in these experiments was 54±4% (Entry 5, n=4) over a duration of 6 days.

The measured $CO_2$ reduction efficiency observed in the current experiments was comparable to the highest demonstrated by *R. eutropha* during $H_2$-fermentation. This biomass yield is equivalent to assimilating about 4.1 mol (180 g) of $CO_2$ captured at the cost of 1 kWh of electricity. The amount of captured $CO_2$ is 1/10 of that caught by amine-based carbon capture and storage (~2000 g at the cost of 1 kWh), but whose processed product cannot be used as a fuel. As shown by the table in FIG. 2, enlarging the batch reactor volume by 10-fold did not perturb the efficiency (Entries 4 and 6), indicating that the system is scalable and the reactor volume does not pose immediate limits. Interestingly, the $\eta_{elec}$ under air (400 ppm $CO_2$) is 20±3% (Entry 7, n=3), which is only 2.7 times lower than the case of pure $CO_2$ in the head space although the partial pressure of $CO_2$ is reduced by 2,500 times. Without wishing to be bound by theory, this indicates that $CO_2$ is not a limiting reagent. The roughly 20% $\eta_{elec}$ for biomass conversion is equivalent to assimilating about 1.5 mol of $CO_2$ captured from about 85,200 liters of air at ambient condition with the cost of 1 kWh of electricity.

Figure 9:
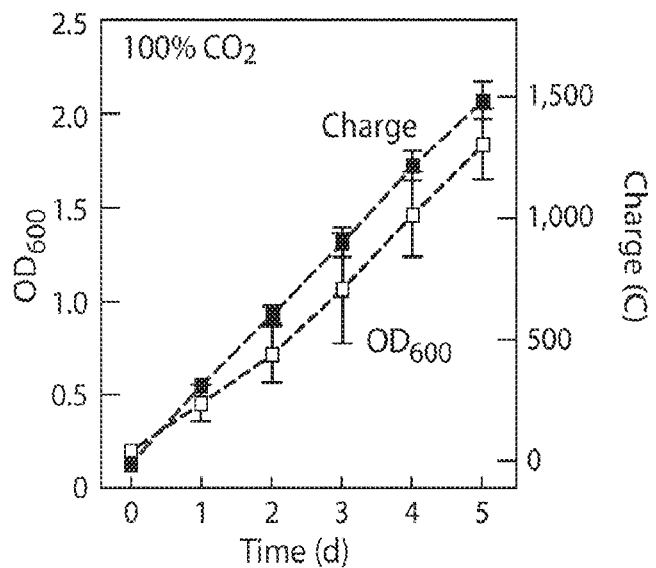
FIG. 9 is a graph of optical density (OD) relative to a calibrated signal for $OD_{600}$ indicating biomass accumulation as well as the cumulative applied electric charge that was passed versus the duration of experiments using a 100% $CO_2$ headspace at 1 atm and an applied potential of 2 V.
Figure 10:
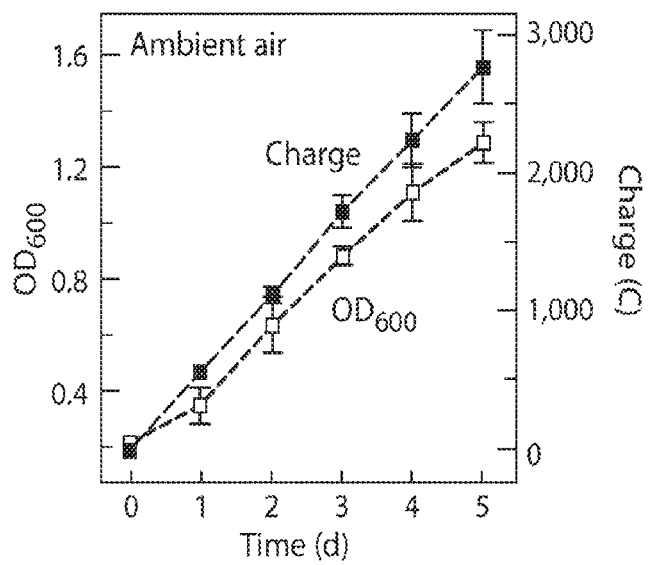
FIG. 10 is a graph of optical density (OD) relative to a calibrated signal for $OD_{600}$ indicating biomass accumulation as well as the cumulative applied electric charge that was passed versus the duration of experiments while exposed to atmospheric air and an applied potential of 2 V.
Figure 11:
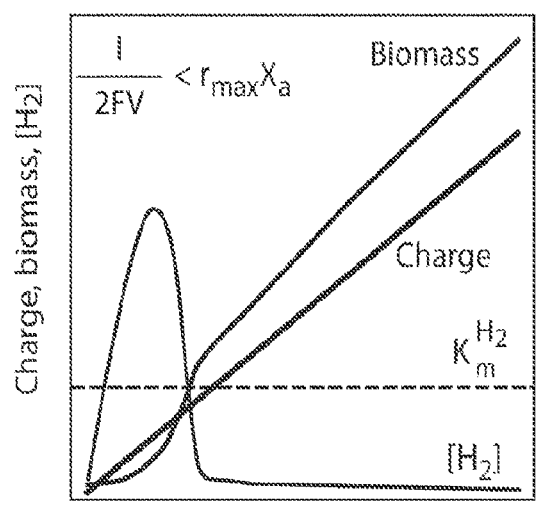
FIG. 11 is a graph of a microbial growth model that predicts linear correlation between electric charges and biomass accumulation.

The current experiments also confirmed that biomass accumulation scales linearly with the amount of charge passed under a pure $CO_2$ head space, FIG. 9 as well as when a batch reactor is exposed to the $CO_2$ levels found in ambient air FIG. 10. Without wishing to be bound by theory, the linear growth is accounted for by a model that combines governing equations for $H_2$-generation from water splitting and biomass accumulation from carbon-fixation. The model predicts a linear correlation between biomass and charge passed after an induction period of low population density of bacteria and high $H_2$ concentration, FIG. 11, which is consistent with the data shown in FIGS. 9 and 10 where the induction period is too short to be observed. Gas chromatography measurements revealed a $H_2$ concentration in the reactor headspace of 0.19±0.04% (n=3) for 100% $CO_2$ and 0.10±0.05% (n=3) in air, which corresponded to 1.5±0.3 and 0.8±0.4 μM in water. These concentrations of $H_2$ are well below the Michaelis constant of about 6 μM for membrane-bound hydrogenases in *R. eutropha*. This may suggest that $H_2$ is facilely consumed by *R. eutropha*. Moreover, similar linear growth conditions for both pure and ambient $CO_2$ atmospheres may indicate that $H_2$ oxidation rather than $CO_2$ reduction is rate-limiting for biosynthesis. Additionally, direct $CO_2$ reduction from air highlights the relatively high affinity of *R. eutropha* for $CO_2$ at low pressures and at high $O_2$ concentrations, in contrast to the previously reported results of synthetic catalysts, individual enzymes, and strictly anaerobic organisms such as acetogens and methanogens.

Figure 12:
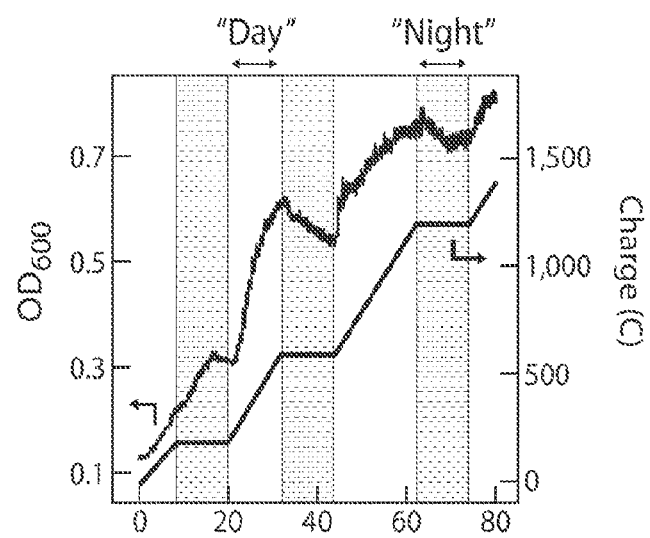
FIG. 12 is a graph of real-time monitoring of biomass accumulation under "day"/"night" cycle testing.

In addition to the above, as shown in FIG. 12, *R. eutropha* halted growth during "night" cycles, when power was not applied to the electrodes similar to what may occur when a system is coupled with a solar power source, and continued $CO_2$ reduction 12 hr later upon resumption of the water-splitting reaction during a corresponding day cycle when power was applied to the electrodes. Specifically, as shown in the figure, the $OD_{600}$ signal decreased during the "dark" phase of the day/night cycle experiments was due to a loss of biomass. Without a source of energy during lithotrophic growth, cells lyse and $OD_{600}$ drops. The observed growth, i.e. increase in biomass, in the first "night" phase may be due to the residual, unconsumed $H_2$ that remains from the previous "day" phase. With higher culture density, there was no excessive $H_2$ in the second and third "night" phases, and $OD_{600}$ subsequently decreased. The differences in biomass loss between the second and third "night" phases is likely due to the conditioning of $H_2$ scarcity as the population grows. These observations confirm the intrinsic dependence of *R. eutropha* on $H_2$ generation. These data also reveal that the $CoP_i|Co-P|R.$ *eutropha* hybrid system are compatible with the intermittent nature of a solar, or other intermittent renewable, energy source.

Example: Catalyst Function

Figure 13:
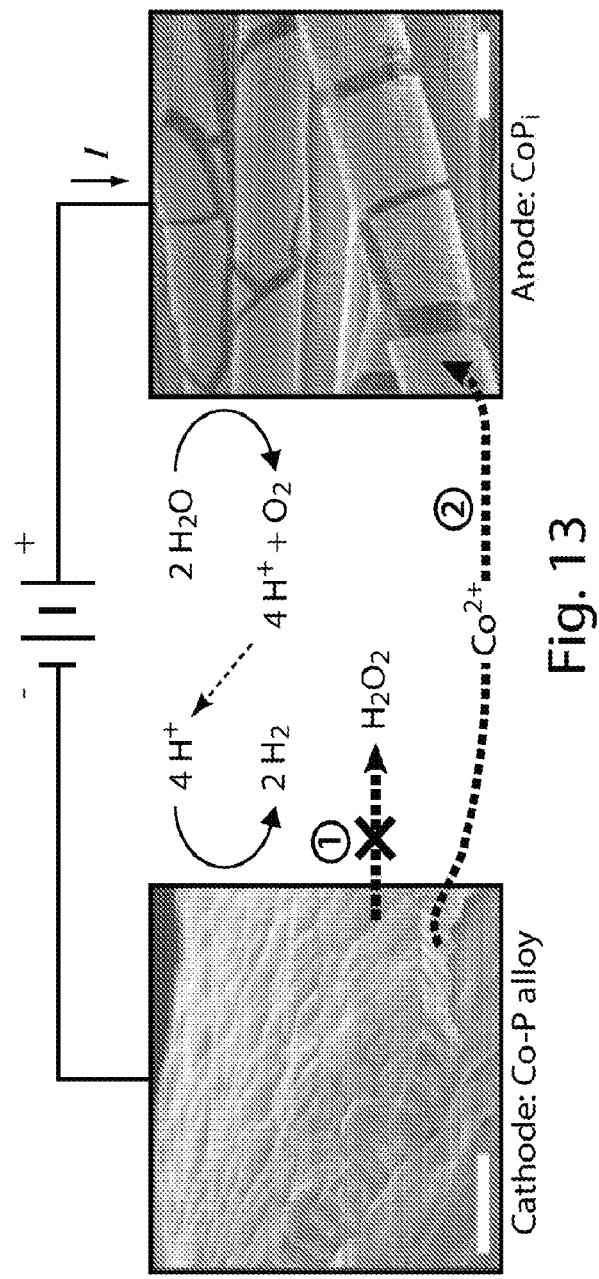
FIG. 13 is a schematic reaction diagram and scanning electron microscopy images for a Co—P alloy cathode and a $CoP_i$ anode with scale bars on the SEM images of 10 μm.

As noted previously, a catalyst including a cobalt phosphorous alloy (Co—P) and a cobalt phosphate ($CoP_i$) may be used. As illustrated in FIG. 13, the Co—P HER and $CoP_i$ OER catalysts work in synergy to form a biocompatible water splitting system that salvages $Co^{2+}$ cations leached from the electrodes, see FIG. 13, via pathway 2 while helping to reduce the production of various reactive oxygen species including $H_2O_2$ along pathway 1.

Figure 14:
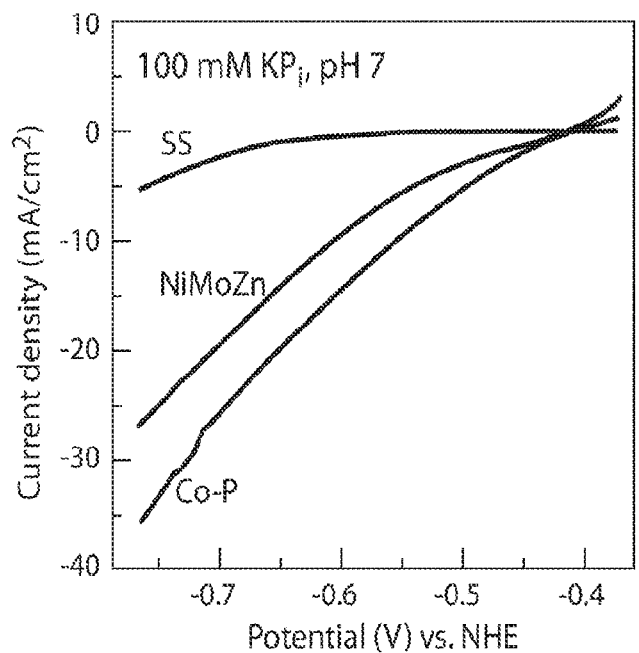
FIG. 14 is a graph of current density versus potential characteristics of different HER catalysts (pH 7, 10 mV/sec)
Figure 15:
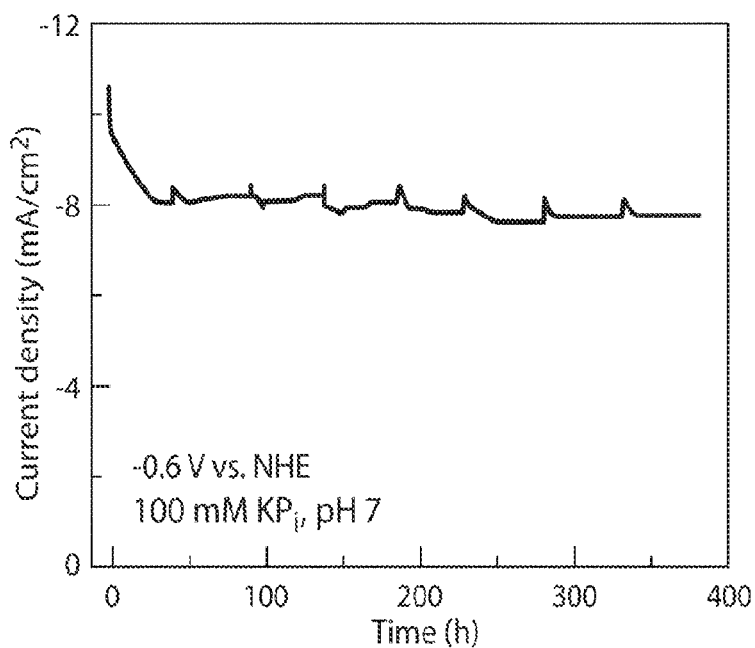
FIG. 15 is a 16-day chronoamperometry graph demonstrating the stability of a Co—P cathode.
Figure 16:
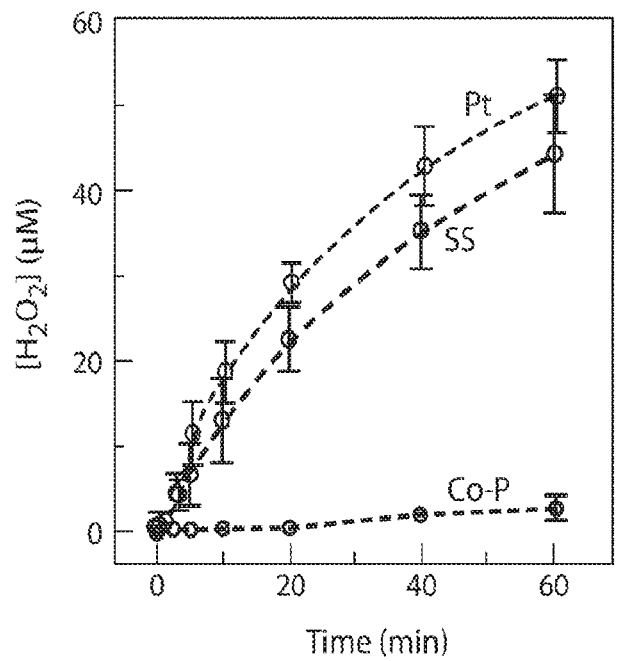
FIG. 16 is a graph of $H_2O_2$ accumulation versus time for various cathodes combined with a $CoP_i$ anode with an $E_{appl}$=2.2 V.

Testing was conducted on the Co—P alloy cathode, which is known to promote HER under alkaline solutions, and exhibits high HER activity in water at neutral pH with minimal ROS production. X-ray photoelectron spectroscopy of Co—P thin films supports the elemental nature of the alloy and energy-dispersive X-ray spectroscopy established a 6 wt % phosphorus composition. The cathode was found to exhibit desirable HER activity in water at neutral pH with a Faradaic efficiency of 99±2%. Moreover, the activity of the Co—P alloy surpassed the activity of the earth-abundant NiMoZn and stainless steel (SS) cathodes used in previous studies, FIG. 14. At constant voltage, a stable HER current was maintained for at least 16 days, see FIG. 15. Negligible $H_2O_2$ was produced during HER as compared to stainless steel (SS) and platinum (Pt) cathodes, see FIG. 16.

Figure 17:
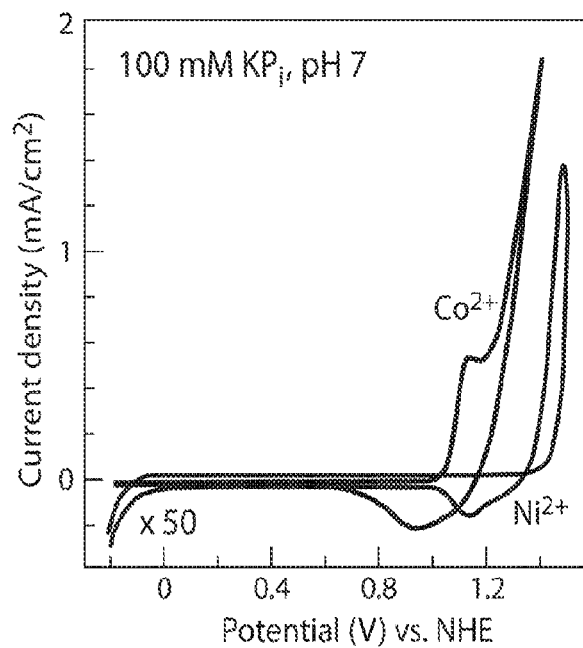
FIG. 17 is a cyclic voltammetry graph of $Co^{2+}$ and $Ni^{2+}$ in the presence of phosphate ($P_i$) with metal concentrations of 0.5 mM and cycled at 50 mV/sec (the curve for $Ni^{2+}$ is magnified by 50 times)
Figure 18:
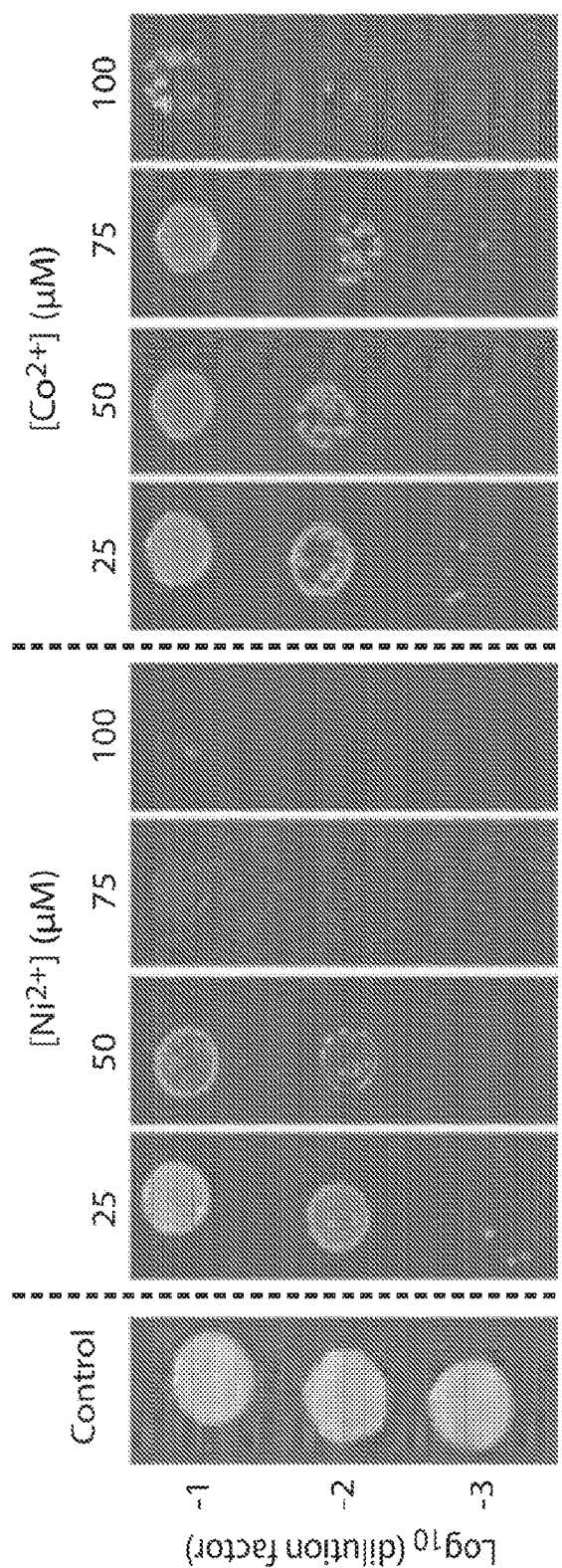
FIG. 18 is a spot assay of R. eutropha in the presence of $Ni^{2+}$ and $Co^{2+}$ at different concentrations.

FIG. 17 presents, cyclic voltammograms of $Co^{2+}$ in the phosphate buffer (pH=7), a pre-wave to the catalytic water-splitting current corresponds to the oxidation of $Co^{2+}$ to $Co^{3+}$, which drives deposition of the catalyst. The $CoP_i$ catalyst is also known to exhibit a deposition rate that is linearly proportional to $Co^{2+}$ concentration. As noted previously, the self-healing property of $CoP_i$ alloy is derived from this interplay of the potential at which OER occurs vs. the potential at which the catalyst deposits. In concert, the Co—P and $CoP_i$ catalysts maintain extremely low concentrations of $Co^{2+}$ in solution through activity derived from the self-healing process. Inductively coupled plasma mass spectrometry (ICP-MS) analysis of a Co-P|$CoP_i$ catalysts system ($E_{appl}$=2.2 V) confirm that sub-µM levels of $Co^{2+}$ are present in solution after 24 h. This concentration of $Co^{2+}$ (0.32±0.06 µM) is well below the concentration of $Co^{2+}$ (half maximal inhibitory concentration, $IC_{50}$ of about 25 µM) that is toxic to R. eutropha as illustrated by the test results shown in FIG. 18. When diffusion between the two electrodes is impeded by a porous glass frit, $Co^{2+}$ concentrations rose to about 50 µM. It is noted for a NiMoZn cathode, $Ni^{2+}$ concentrations are not regulated by self-healing as $NiP_i$ cannot form from $P_i$, and the deposition to $NiO_x$ occurs at >1.5 V vs. NHE as also shown in FIG. 17.

Example: Growth Under Nutrient Constraints

Figure 19:
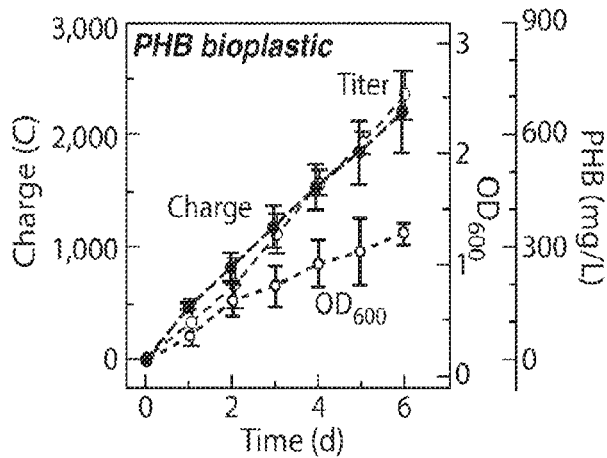
FIG. 19 is a graph of Optical Density, concentrations of PHB, and charges passed through the electrodes plotted vs. duration at 24 hr intervals.
Figure 20:
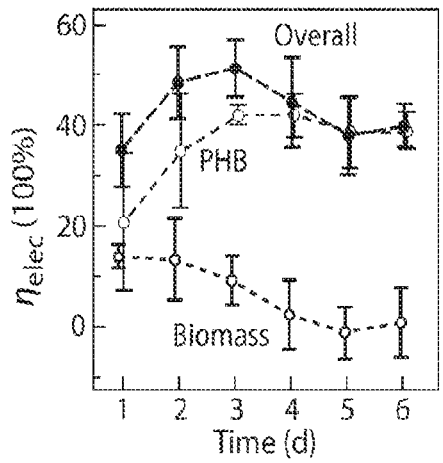
FIG. 20 is a graph of the averaged $\eta_{elec}$ for biomass, PHB, and the overall $\eta_{elec}$ combining biomass and chemical formation at 24 hr intervals.
Figure 21:
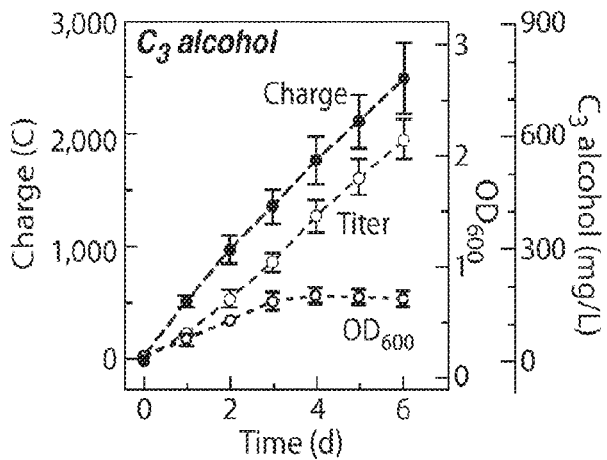
FIG. 21 is a graph of Optical Density, concentrations of $C_3$ alcohol, and charges passed through the electrodes are plotted vs. duration at 24 hr intervals.
Figure 22:
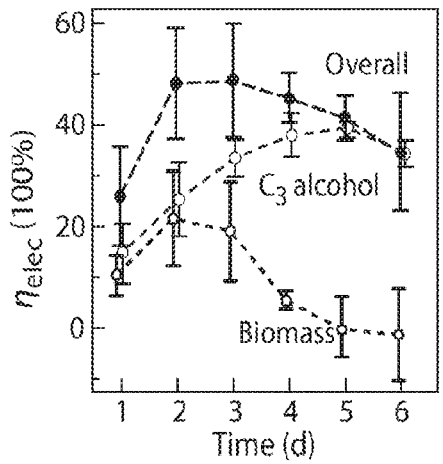
FIG. 22 is a graph of the averaged $\eta_{elec}$ for biomass, $C_3$ alcohol, and the overall $\eta_{elec}$ combining biomass and chemical formation at 24 hr intervals.
Figure 23:
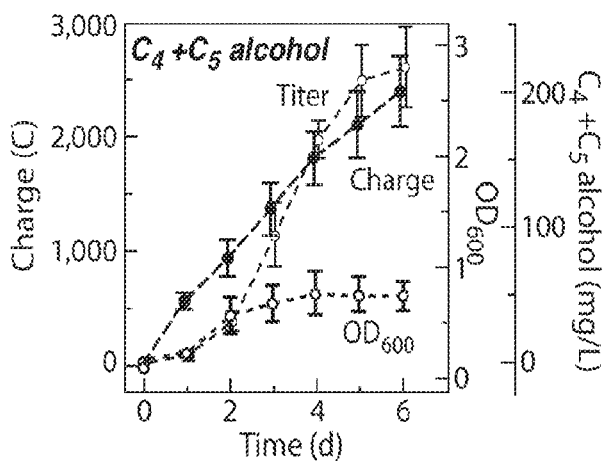
FIG. 23 is a graph of Optical Density, concentrations of $C_4+C_5$ alcohol, and charges passed through the electrodes are plotted vs. duration at 24 hr intervals.
Figure 24:
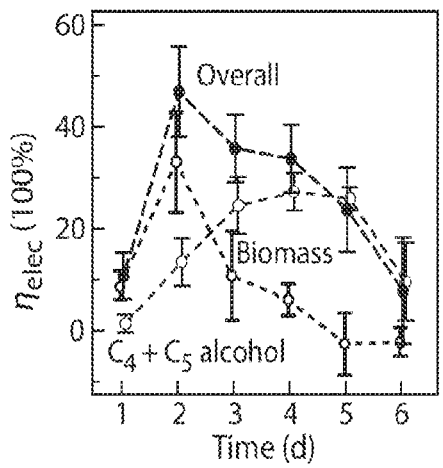
FIG. 24 is a graph of the averaged $\eta_{elec}$ for biomass, $C_4+C_5$ alcohol, and the overall $\eta_{elec}$ combining biomass and chemical formation at 24 hr intervals.

Metabolic engineering of R. eutropha enables the renewable production of an array of fuels and chemical products. Specifically, when R. eutropha confronts nutrient constraints coupled with carbon excess, the biosynthesis of poly(3-hydroxybutyrate) (PHB) is triggered in the wild-type H16 strain as an internal carbon storage, see FIG. 1B. As such, digestion is used for PHB collection. Under a constant rate of water splitting, PHB synthesis was not manifest until nitrogen became limiting at around 2 days, indicated by the cessation of biomass accumulation, see FIG. 19, as well as the $\eta_{elec}$ taken every 24 hours shown in FIG. 20. Using a titer of about 700 mg/L, the 6-d average for PHB synthesis was measured to be $\eta_{elec}$=36±3%, see FIG. 6, with a 24-h maximum of $\eta_{elec}$=42±2% (n=3) see FIG. 20. In engineered strains, this PHB pathway can be modified to excrete the fusel alcohols isopropanol ($C_3$), isobutanol ($C_4$), and 3-methyl-1-butanol ($C_5$) with energy densities of 24, 28, and 31 MJ/L, respectively as well as other possible products. The culture supernatant was analyzed to quantify the secreted alcohols. The accumulation of these liquid fuels follows similar trends as observed for PHB synthesis. FIGS. 21 and 23 show that biomass production plateaus while isopropanol titers grow to about 600 mg/L and $C_4$+$C_5$ alcohol titers grow to about 220 mg/L. Engineered R. eutropha strain produced isopropanol with a 6-day average $\eta_{elec}$=31±4%, FIG. 6, with a 24-hr maximum of $\eta_{elec}$=39±2% (n=4), FIG. 22. The bacterial strain engineered to produce $C_4$+$C_5$ alcohols averaged a 6-day $\eta_{elec}$=16±2%, FIG. 6, with a 24-hr maximum of $\eta_{elec}$=27±4% (n=3), FIG. 24. The achieved titers were higher than previously reported values, and $\eta_{elec}$ have been increased by at least 20 to 50 fold compared to previously reported results.

Figure 25:
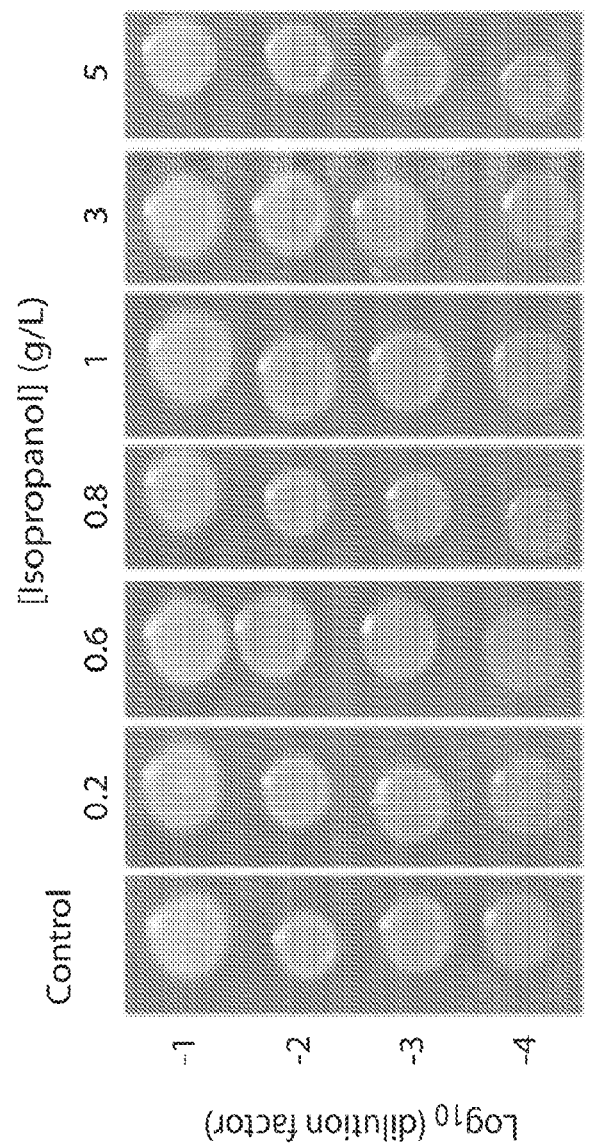
FIG. 25 is a spot assay of the tolerance of R. eutropha versus different concentrations of isopropanol.

FIG. 25 is a photograph of cell cultures taken for different isopropanol concentration. As illustrated by the cultures, R. eutropha demonstrates tolerance towards isopropanol, which allows for enriched product concentrations under extended operation and is consistent with the observed system behavior described above regarding continued production and cell growth with increasing isopropanol concentrations.

Example: Reactive Oxygen Species (ROS) Resistance

Figure 26:
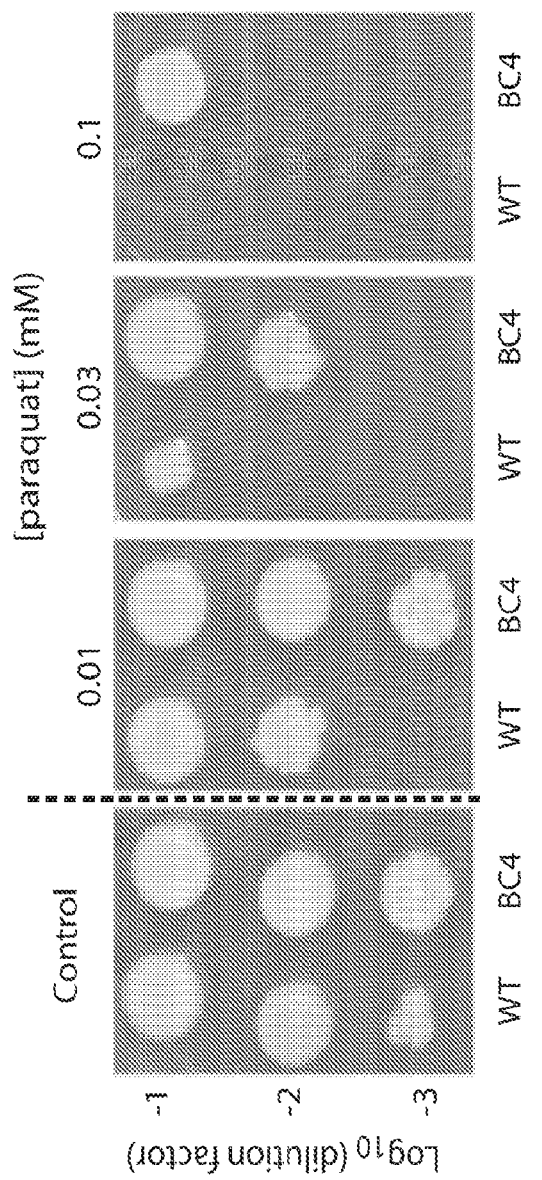
FIG. 26 is a spot assay illustrating the reactive oxygen species (ROS) tolerance between $H_{16}$ and ROS-resistant BC4 strains of R. eutropha bacteria.

A ROS-resistant variant of R. eutropha, evolved from a reactor including a stainless steel $CoP_i$ water-splitting electrode pair after 11 consecutive days of operation at an applied voltage potential of 2.3 V with a $H_2O_2$ generation rate of ~0.6 µM/min. Genome sequencing found several mutations between the strain (BC4) and the wild-type (H16) described above in reference to Table I. In the presence of paraquat as a ROS-inducer, the $IC_{50}$ of paraquat for BC4 is almost one order of magnitude higher than that of wild type, see FIG. 26. However, there was minimal difference noted in $\eta_{elec}$ for the current reactor systems using the Co-P|$CoP_i$ electrode pairs, confirming minimal concentrations of ROS in the reactors. Of course, it should be understood that BC4 may be used in any reactor system, and may also be beneficial for use in helping systems achieve a high $\eta_{elec}$ where ROS are present in larger concentrations.

Example: Conversion Efficiencies

As noted above, the combined systems, catalysts, and bacteria described herein, and illustrated in the experiments above, help to mitigate biotoxicity at a systems level while also providing bacteria resistance to the various toxicants present in the system, thus, allowing water-splitting catalysis to be interfaced with engineered organisms to realize high $CO_2$ reduction efficiencies that exceed natural photosynthetic systems. Owing to low $E_{appl}$ of 1.8-2.0 V for water splitting, high $\eta_{elec}$ are achieved that translate directly to high solar-to-chemical efficiencies ($\eta_{SCE}$) when coupled to typical solar-to-electricity device ($\eta_{SCE}=\eta_{solar}\times\eta_{elec}$). For a photovoltaic device of $\eta_{solar}$=18%, the Co-P|$CoP_i$|R. eutropha hybrid system can achieve at least a $\eta_{SCE}$=9.7% for biomass, 7.6% for bio-plastic, and 7.1% for fusel alcohols. This approach allows for the development of artificial photosynthesis with efficiencies well beyond natural photosynthesis, thus providing a platform for the distributed solar production of chemicals.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method comprising:
splitting water using a cathode including a cobalt-phosphorus alloy and an anode including cobalt phosphate in a solution containing a chemolithoautotrophic bacteria to form hydrogen ($H_2$) and oxygen ($O_2$) in the solution;
providing carbon dioxide ($CO_2$) in the solution;
providing bioavailable nitrogen in the solution;
maintaining the bioavailable nitrogen in the solution to below a threshold nitrogen concentration to control production of a product by the chemolitoautrophic bacteria.

2. The method of claim 1, wherein the chemolithoautotrophic bacteria is a *Ralstonia eutropha* bacteria.

3. The method of claim 1, wherein the chemolithoautotrophic bacteria is resistant to reactive oxygen species.

4. The method of claim 1, wherein the product is an alcohol.

5. The method of claim 1, wherein the product is at least one of a fatty acid, an alkane, a polyhydroxyalkanoate, and an amino acid.

6. The method of claim 1, wherein the solution includes a phosphate.

7. The method of claim 1, further comprising continuously bubbling carbon dioxide through the solution.

8. The method of claim 1, further comprising maintaining an isolated gas volume above a surface of the solution within a head space of a reactor chamber.

9. The method of claim 8, further comprising replenishing the isolated gas volume to an original composition at one or more time intervals.

10. The method of claim 8, wherein the isolated gas volume comprises primarily carbon dioxide.

11. The method of claim 1, wherein splitting of the water is controlled to generate hydrogen at a rate equal to a rate of hydrogen consumption by the bacteria.

12. The method of claim 1, wherein the solution is disposed in a reactor chamber.

13. The method of claim 8, wherein maintaining the composition of the isolated gas volume within the head space maintains the concentration of the bioavailable nitrogen in the solution below the threshold nitrogen concentration.

14. The method of claim 1, further comprising sensing a concentration of one or more gases dissolved in the solution, and controlling the concentration of the one or more gases dissolved in the solution based at least in part on the sensed concentration of the one or more gases dissolved in the solution.

15. The method of claim 14, further comprising changing the concentration of the one or more gases dissolved in the solution to be within a predetermined range based at least in part on the sensed concentration of the one or more gases dissolved in the solution.

16. The method of claim 14, wherein the one or more gases includes hydrogen, and further comprising changing a generation rate of hydrogen by the cathode and the anode to control the concentration of hydrogen in the solution.

17. The method of claim 14, wherein the one or more gases dissolved in the solution includes nitrogen gas dissolved in the solution.

18. A method comprising:
splitting water using a cathode including a cobalt-phosphorus alloy and an anode including cobalt phosphate in a solution containing a chemolithoautotrophic bacteria to form hydrogen ($H_2$) and oxygen ($O_2$) in the solution, and wherein the solution includes bioavailable nitrogen.

19. The method of claim 18, further comprising providing carbon dioxide ($CO_2$) in the solution.

20. The method of claim 18, further comprising continuously bubbling carbon dioxide through the solution.

21. The method of claim 18, further comprising maintaining the bioavailable nitrogen in the solution to below a threshold nitrogen concentration to control production of a product by the chemolitoautrophic bacteria.

22. The method of claim 18, wherein the chemolithoautotrophic bacteria is a *Ralstonia eutropha* bacteria.

23. The method of claim 18, wherein the chemolithoautotrophic bacteria is resistant to reactive oxygen species.

24. The method of claim 18, wherein the product is an alcohol.

25. The method of claim 18, wherein the product is at least one of a fatty acid, an alkane, a polyhydroxyalkanoate, and an amino acid.

26. The method of claim 18, wherein the solution includes a phosphate.

27. The method of claim 18, further comprising maintaining an isolated gas volume above a surface of the solution within a head space of a reactor chamber.

28. The method of claim 27, further comprising replenishing the isolated gas volume to an original composition at one or more time intervals.

29. The method of claim 27, wherein the isolated gas volume comprises primarily carbon dioxide.

30. The method of claim 27, wherein maintaining the composition of the isolated gas volume within the head space maintains the concentration of the bioavailable nitrogen in the solution below a threshold nitrogen concentration.

31. The method of claim 18, wherein splitting of the water is controlled to generate hydrogen at a rate equal to a rate of hydrogen consumption by the bacteria.

32. The method of claim 18, wherein the solution is disposed in a reactor chamber.

33. The method of claim 18, further comprising sensing a concentration of one or more gases dissolved in the solution, and controlling the concentration of the one or more gases dissolved in the solution based at least in part on the sensed concentration of the one or more gases dissolved in the solution.

34. The method of claim 33, further comprising changing the concentration of the one or more gases dissolved in the solution to be within a predetermined range based at least in part on the sensed concentration of the one or more gases dissolved in the solution.

35. The method of claim 33, wherein the one or more gases includes hydrogen, and further comprising changing a generation rate of hydrogen by the cathode and the anode to control the concentration of hydrogen in the solution.

36. The method of claim 33, wherein the one or more gases dissolved in the solution includes nitrogen gas dissolved in the solution.

* * * * *

SEQUENCE LISTING

<160> NUMBER OF SEQ ID NOS: 4

<210> SEQ ID NO 1

```
<211> LENGTH: 209
<212> TYPE: DNA
<213> ORGANISM: Artificial Sequence
<220> FEATURE:
<223> OTHER INFORMATION: Synthetic polynucleotide

<400> SEQUENCE: 1
gcctcgctgc tttccacctg gcgccgcacg cggccccaga cgtcgatttc ccaggttgcg      60
cccagggtcg cgctctgccc gttgagcgtg ctgccgctgg cgccgcgcgc gcgcgaggcg     120
ccggcctgtg cgtcgacggt cgggaagaag ccggcgcgcg cggcctgcag cgacgccacc     180
gcctggcggt actgcgcctc ggcggcctt                                       209

<210> SEQ ID NO 2
<211> LENGTH: 1495
<212> TYPE: DNA
<213> ORGANISM: Artificial Sequence
<220> FEATURE:
<223> OTHER INFORMATION: Synthetic polynucleotide

<400> SEQUENCE: 2
aggcgccggc ctgtgcgtcg acggtcggga agaagccggc gcgcgcggcc tgcagcgacg      60
ccaccgcctg gcggtactgc gcctcggcgg ccttgatgtt ctggttcgag atctgcacct     120
cggacatcag cgcgtcgagc tgcgcatcgc cgaacacggt ccaccagtcg gcgcgtgcca     180
gcgcatcctg cggctcggcg ggcttccagt cgccggtcca ggcggggggtg gcggcatcgg     240 cttccttgaa ggatgcggaa accggcgcgt cggggcgctg gtagtcgggg ccgacggcgc     300
agccggccca cagcagcgcg caggccagcg acaccggcag gcatgggtc aggaggcggg      360 aaagaactgt catgtcgagt cttcgcaaat ctagacggcg gccggctggt caggcgtgcc     420
ggcaccacgg cggcgctggc gccaggcctt gaccttcagg cgccagcggt ccagcgtcag     480
gtagaccacc ggcgtggtgt acagcgtcag cagctggctt accaccagtc gccgacaat     540 ggagatgccc agcggcgcgc gcagttcggc gccgtcgccg cggccgattg ccagcggcac     600
cgcgcccagc agcgcggcca tggtggtcat caggatcggg cggaagcgca gcaggcaggc     660
gcggtagatc gcgtcgcgcg cgacaggcc atcgcgccgt tcggcatcga tggcgaagtc      720
gatcatcatg atcgcgttct ttttcacgat gccgatcagc aggatcacgc cgatcagcgc     780
gatgatgctg aagtcggtct tcgatgccag cagcgccagc agcgcgccca cgccggcgga     840
gggcagcgtc gacaggatcg tcagcggatg cacatagctt tcatacagca cgcccagcac     900
gatgtagatc gtgatcagcg ccgccaggat caggatcggc tgactcttga gcgaatcctg     960
gaacgccttg gcgccgccct ggaagttggc gcgcagcgtc tccggcacgc cgatgcgcgc    1020
catctcgcgc gtgatcgcgt cggtcgcctg cgacagcgaa gtgccctcgg ccaggttgaa    1080
cgagatcgtc gaggccgcga actggccctg gtggttcacg cccagcggcg tgctggacgg    1140
ggtcacgcgc gcgaacgccg ccagcggcac gcggttgccg ttgccggtga ccacgtagat    1200
gtccttgagc gcatcgggcc cttgcaggta ttcctggctc agctccatca ccacgcggta    1260
ctggttcagc ggatggtaga tggtggacac cagccgctgg ccgaaggcat cgttgagcac    1320
cgcatccacc tgctgcgcgg tcacgcccag gcgcgaggcc gcgtcgcggt cgatgatcac    1380
cgaggtctgc aggcccttgt cgttggtatc ggtgtcgata tcctccagcc ccttcaggtt    1440
cgacaacgcg gcgcgcacct tgggctccca cgcgcgcagc acttccaggt cgtcc          1495

<210> SEQ ID NO 3
<211> LENGTH: 201
```

```
<212> TYPE: DNA
<213> ORGANISM: Artificial Sequence
<220> FEATURE:
<223> OTHER INFORMATION: Synthetic polynucleotide

<400> SEQUENCE: 3
gcagcttgat gccattgacg aggtagatgg aaaccggcac gtgctctttg cgcagcgcgt      60
tcaggaacgg gccttgtagc agttgccctt tgttgctcat ggcacactcc aaatttatag     120
gtttagtggt gaatgatggg gatggaaatc cccggttcaa gtcaggcggc gcaaaaacgc     180
gccagaaaaa agatcaaaaa c                                               201

<210> SEQ ID NO 4
<211> LENGTH: 479
<212> TYPE: DNA
<213> ORGANISM: Artificial Sequence
<220> FEATURE:
<223> OTHER INFORMATION: Synthetic polynucleotide

<400> SEQUENCE: 4
gaggatgcca tgtccgaagc gcctgtcctt gccccctcga cctcaaccca gccgcccgcc      60
gccggccagc tcaacctgat ccgcccgcag ccatatgccg actgggcgcc gcaggtcacg     120
gccgaagaac gcgccacgct gcgccgcgag ctggagcagg gcgccgtgct gtacttcccg     180
aacctgaatt tccgcttcca gccgggcgaa gagcgcttcc ttgacagccg ctattccgac     240
ggcaagtcca agaacatcaa cctgcgcgcc gacgacaccg cggtgcgcgg cgcccagggc     300
agtccgcagg acctggcgga cctgtacacg ctgatccgcc gctacgccga caacagcgaa     360
ttgctggtgc gcacgctgtt ccctgaatac atcccgcaca tgacgcgcgc cggcacctcg     420
ctgcggccca gcgagatcgc cgggcgcccg gtcagctggc gcaaggacga cacccgcct      479
```